(12) United States Patent
Hong et al.

(10) Patent No.: US 10,595,888 B2
(45) Date of Patent: Mar. 24, 2020

(54) SELF-CLOSING DEVICES AND APPARATUS AND METHODS FOR MAKING AND DELIVERING THEM

(71) Applicant: Solinas Medical Inc., Santa Clara, CA (US)

(72) Inventors: James Hong, Sunnyvale, CA (US); Amy Lee, Sunnyvale, CA (US); Erik van der Burg, Los Gatos, CA (US)

(73) Assignee: SOLINAS MEDICAL INC., Santa Clara, CA (US)

( * ) Notice: Subject to any disclaimer, the term of this patent is extended or adjusted under 35 U.S.C. 154(b) by 846 days.

(21) Appl. No.: 14/882,322

(22) Filed: Oct. 13, 2015

(65) Prior Publication Data

US 2016/0199085 A1 Jul. 14, 2016

Related U.S. Application Data

(63) Continuation of application No. PCT/US2014/033892, filed on Apr. 12, 2014.

(Continued)

(51) Int. Cl.
*A61M 39/02* (2006.01)
*A61F 2/962* (2013.01)
(Continued)

(52) U.S. Cl.
CPC .......... *A61B 17/32* (2013.01); *A61B 17/0057* (2013.01); *A61F 2/07* (2013.01);
(Continued)

(58) Field of Classification Search
CPC ... A61M 39/02; A61F 2002/075; A61F 2/962; A61F 2/95; A61F 2/92; A61F 2/89;
(Continued)

(56) References Cited

U.S. PATENT DOCUMENTS 3,814,137 A 6/1974 Martinez
4,428,364 A * 1/1984 Bartolo ..................... A61F 2/12
128/897

(Continued)

FOREIGN PATENT DOCUMENTS

CN 101384228 A 3/2009
EP 1649888 4/2006
(Continued)

OTHER PUBLICATIONS

Korean Intellectual Property Office, International Search Report for corresponding International Application No. PCT/US2014/033892, Applicant: Solinas Medical, Inc., Form PCT/ISA/210, dated Aug. 28, 2014, 4 pages.

(Continued)

*Primary Examiner* — Jacob J Cigna
(74) *Attorney, Agent, or Firm* — William A. English; Vista IP Law Group LLP

(57) ABSTRACT

A self-closing device for implantation within a patient's body includes base material including an inner surface area for securing the base material to a tissue structure, and a plurality of support elements surrounding or embedded in the base material. The support elements are separable to accommodate creating an opening through the base material for receiving one or more instruments through the base material, and biased to return towards a relaxed state for self-closing the opening after removing the one or more instruments. The device may be provided as a patch, cuff, or integrally attached to a tubular graft or in various shapes.

14 Claims, 12 Drawing Sheets

Related U.S. Application Data

(60) Provisional application No. 61/811,733, filed on Apr. 13, 2013, provisional application No. 61/811,719, filed on Apr. 13, 2013.

(51) Int. Cl.
*A61F 2/95* (2013.01)
*A61F 2/89* (2013.01)
*A61B 17/32* (2006.01)
*A61F 2/92* (2013.01)
*A61F 2/07* (2013.01)
*A61B 17/00* (2006.01)
*A61F 17/00* (2006.01)

(52) U.S. Cl.
CPC .................. *A61F 2/89* (2013.01); *A61F 2/92* (2013.01); *A61F 2/95* (2013.01); *A61F 2/962* (2013.01); *A61M 39/02* (2013.01); *A61B 2017/0061* (2013.01); *A61B 2017/00526* (2013.01); *A61B 2017/00623* (2013.01); *A61B 2017/00659* (2013.01); *A61B 2017/00676* (2013.01); *A61B 2017/00867* (2013.01); *A61B 2017/320044* (2013.01); *A61F 2002/075* (2013.01)

(58) Field of Classification Search
CPC ........... A61F 2/07; A61B 2017/320044; A61B 2017/00867; A61B 2017/00676; A61B 2017/00659; A61B 2017/00623; A61B 2017/0061; A61B 2017/00526; A61B 17/32; A61B 17/0057
See application file for complete search history.

(56) References Cited

U.S. PATENT DOCUMENTS

| | | |
|---|---|---|
| 4,564,915 A | 1/1986 | Evans et al. |
| 4,619,641 A | 10/1986 | Shanzer |
| 4,645,495 A | 2/1987 | Vaillan-court |
| 4,816,339 A | 3/1989 | Tu et al. |
| 5,059,486 A * | 10/1991 | Maronian ................. A61F 6/02 264/288.4 |
| 5,100,422 A | 3/1992 | Berguer et al. |
| 5,562,617 A | 10/1996 | Finch, Jr. et al. |
| 5,647,855 A | 7/1997 | Trooskin |
| 5,713,859 A | 2/1998 | Finch, Jr. et al. |
| 5,725,507 A * | 3/1998 | Petrick ................. A61M 5/152 215/247 |
| 5,755,769 A | 5/1998 | Richard et al. |
| 5,800,512 A | 9/1998 | Lentz |
| 5,866,217 A | 2/1999 | Stenoien et al. |
| 5,906,596 A | 5/1999 | Tallarida |
| 5,931,865 A | 8/1999 | Silverman et al. |
| 5,944,688 A | 8/1999 | Lois |
| 5,984,955 A | 11/1999 | Wisselink |
| 6,004,348 A * | 12/1999 | Banas ....................... A61F 2/07 606/198 |
| 6,007,516 A | 12/1999 | Burbank |
| 6,053,943 A * | 4/2000 | Edwin ....................... A61F 2/07 600/36 |
| 6,149,681 A | 11/2000 | Houser et al. |
| 6,261,257 B1 | 7/2001 | Uflacker et al. |
| 6,319,279 B1 | 11/2001 | Shannon |
| 6,436,135 B1 | 8/2002 | Goldfarb |
| 6,553,167 B2 | 4/2003 | Hurley et al. |
| 6,565,599 B1 * | 5/2003 | Hong ....................... A61F 2/91 623/1.15 |
| 6,582,409 B1 | 6/2003 | Squitieri |
| 6,645,242 B1 | 11/2003 | Quinn |
| 6,790,225 B1 | 9/2004 | Shannon et al. |
| 6,962,577 B2 | 11/2005 | Tallarida et al. |
| 7,056,336 B2 | 6/2006 | Armstrong |
| 7,255,682 B1 | 8/2007 | Bartol et al. |
| 7,261,705 B2 | 8/2007 | Edoga et al. |
| 7,438,721 B2 | 10/2008 | Doig |
| 7,452,374 B2 | 11/2008 | Hain |
| 7,727,143 B2 | 6/2010 | Birk et al. |
| 7,762,977 B2 | 7/2010 | Porter et al. |
| 7,780,590 B2 | 8/2010 | Birk et al. |
| 7,914,438 B2 | 3/2011 | Buckberg et al. |
| 8,079,973 B2 | 12/2011 | Herrig et al. |
| 8,163,002 B2 | 4/2012 | Weinberg |
| 8,210,084 B2 * | 7/2012 | An ........................... A61F 2/90 87/13 |
| 8,313,524 B2 | 11/2012 | Edwin et al. |
| 8,414,530 B2 | 4/2013 | Mason |
| 8,679,150 B1 * | 3/2014 | Janardhan ........ A61B 17/22031 606/200 |
| 8,906,087 B2 | 12/2014 | House et al. |
| 9,440,058 B2 * | 9/2016 | Osborne ........... A61M 39/0208 |
| 9,545,300 B2 * | 1/2017 | Cully ................. A61B 17/0057 |
| 2002/0188318 A1 | 12/2002 | Carley et al. |
| 2003/0100920 A1 | 5/2003 | Akin et al. |
| 2004/0098089 A1 | 5/2004 | Weber |
| 2004/0127970 A1 * | 7/2004 | Saunders ................... A61F 2/91 623/1.15 |
| 2004/0186377 A1 * | 9/2004 | Zhong ................... A61M 25/00 600/431 |
| 2005/0131520 A1 | 6/2005 | Zilla et al. |
| 2006/0025848 A1 | 2/2006 | Weber et al. |
| 2006/0106406 A1 | 5/2006 | Weinberger |
| 2006/0136043 A1 * | 6/2006 | Cully ................. A61B 17/0057 623/1.22 |
| 2006/0281966 A1 | 12/2006 | Peacock |
| 2007/0088336 A1 | 4/2007 | Dalton |
| 2007/0106375 A1 | 5/2007 | Vonderwalde |
| 2007/0123968 A1 | 5/2007 | Weinberg |
| 2007/0167901 A1 | 7/2007 | Herrig et al. |
| 2007/0213838 A1 | 9/2007 | Hengel-molen |
| 2007/0265584 A1 | 11/2007 | Hickman et al. |
| 2007/0299538 A1 | 12/2007 | Roeber |
| 2008/0009889 A1 | 1/2008 | Pokorney et al. |
| 2008/0114444 A1 | 5/2008 | Yu |
| 2008/0140182 A1 * | 6/2008 | Scheller .................... A61F 2/07 623/1.17 |
| 2008/0194905 A1 | 8/2008 | Walsh |
| 2008/0243080 A1 | 10/2008 | Chang |
| 2009/0157014 A1 * | 6/2009 | Osborne ........... A61M 39/0208 604/264 |
| 2009/0234431 A1 | 9/2009 | Weinberger |
| 2010/0130995 A1 | 5/2010 | Yevzlin |
| 2010/0292774 A1 | 11/2010 | Shalev |
| 2011/0295181 A1 | 12/2011 | Dann et al. |
| 2011/0307059 A1 | 12/2011 | Young |
| 2012/0058249 A1 * | 3/2012 | House ..................... A61L 27/16 427/2.25 |
| 2012/0310324 A1 | 12/2012 | Benary et al. |
| 2013/0060268 A1 | 3/2013 | Herrig |
| 2013/0090723 A1 | 4/2013 | Cully et al. |
| 2013/0102840 A1 * | 4/2013 | Franklin ........... A61M 39/0208 600/37 |
| 2013/0103135 A1 | 4/2013 | Vinluan |
| 2013/0237929 A1 * | 9/2013 | Hong ................. A61B 17/0057 604/264 |
| 2014/0172074 A1 * | 6/2014 | Concagh ................... A61F 2/90 623/1.19 |
| 2014/0180190 A1 | 6/2014 | Dann et al. |
| 2014/0222069 A1 * | 8/2014 | Carley ............... A61B 17/0057 606/213 |
| 2015/0025437 A1 | 1/2015 | Tomko et al. |
| 2015/0327844 A1 | 11/2015 | Hong et al. |
| 2017/0020644 A1 | 1/2017 | Taylor |

FOREIGN PATENT DOCUMENTS

| | | |
|---|---|---|
| WO | 9846115 A2 | 10/1998 |
| WO | 2007061787 A2 | 5/2007 |
| WO | 2010015001 | 2/2010 |

(56) References Cited

FOREIGN PATENT DOCUMENTS

WO      2011112755 A2     9/2011
WO      WO-2011112755 A2 *   9/2011   ......... A61B 17/0057

OTHER PUBLICATIONS

Korean Intellectual Property Office, International Preliminary Report on Patentability for corresponding International Application No. PCT/US2014/033892, Applicant: Solinas Medical, Inc.,Forms PCT/IB/373 and PCT/ISA/237 dated Aug. 27, 2014, 14 pages.
Kita-Aoyama International Patent Bureau, Office Action and translation from corresponding Japanese application No. 2016-507697, Applicant: Solinas Medical, Inc., dated Mar. 13, 2018, 6 pages.
Assion, Jean-Charles, European Patent Office Examination Report for Corresponding European Patent Application No. 14783249.7-1122, dated Jun. 17, 2019, 4 pages.

* cited by examiner

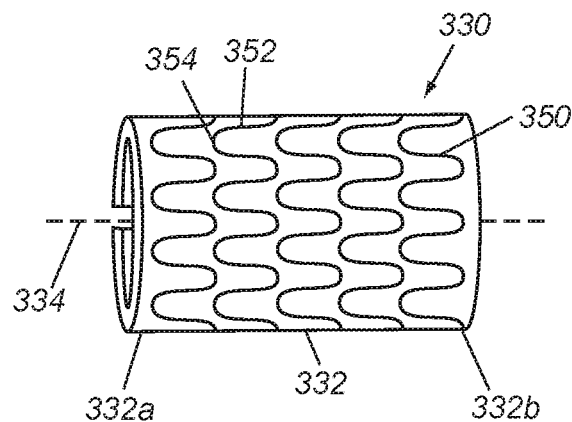
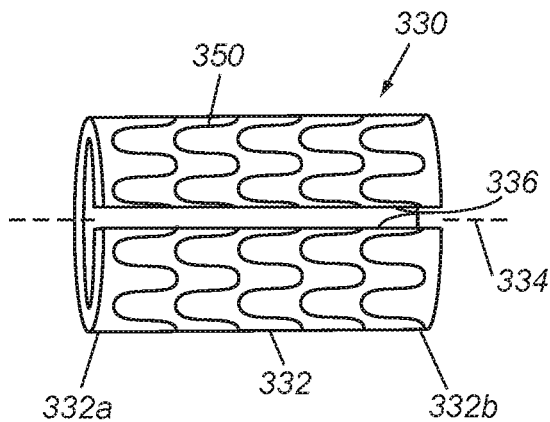
FIG. 1A  FIG. 1B
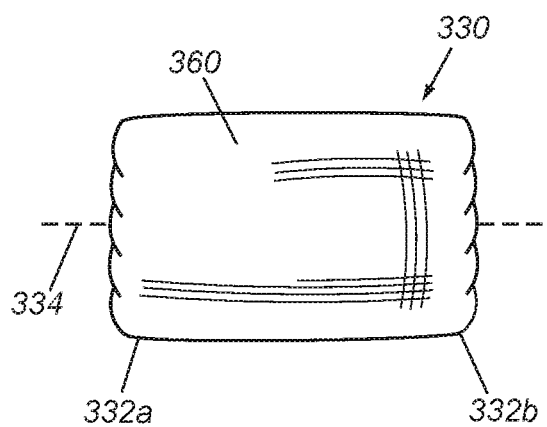
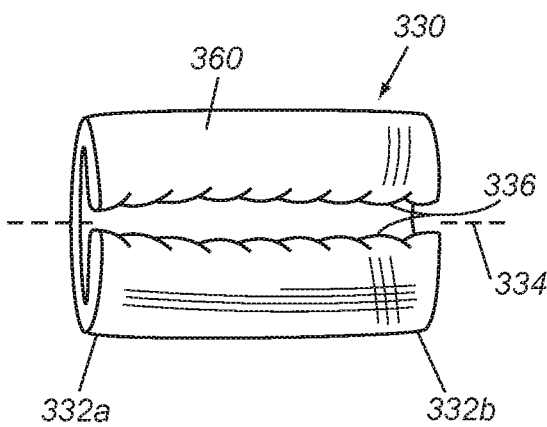
FIG. 2A  FIG. 2B
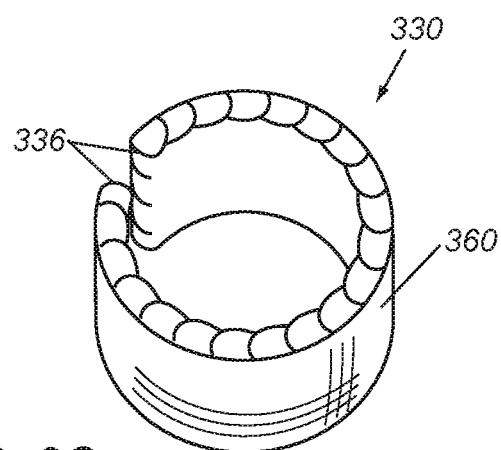
FIG. 2C

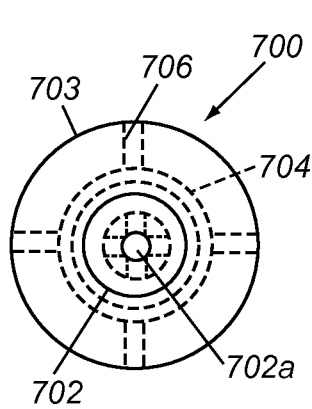
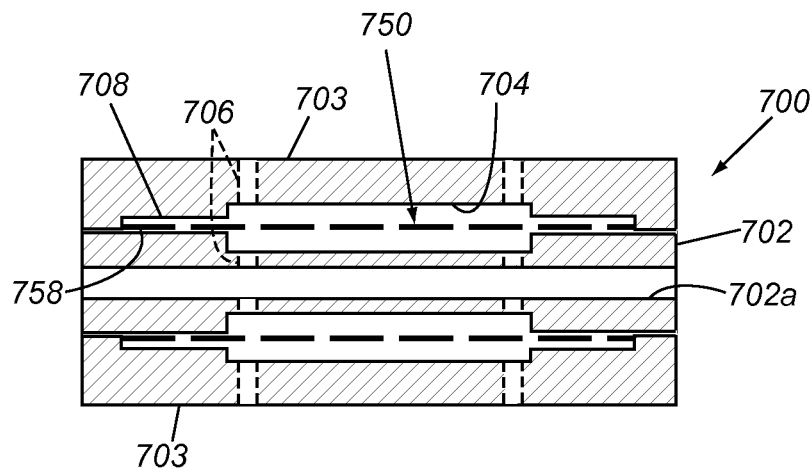
FIG. 11A  FIG. 11B
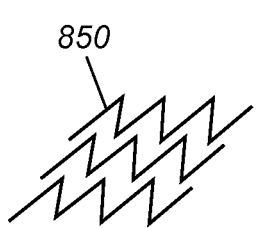
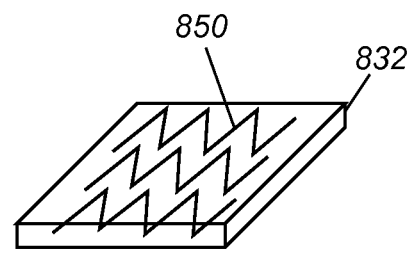
FIG. 12A  FIG. 12B
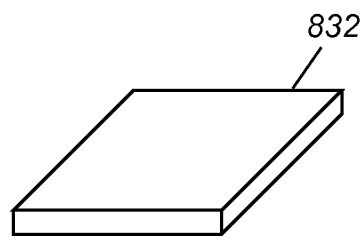
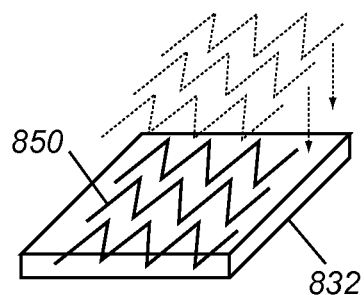
FIG. 12C  FIG. 12D

SELF-CLOSING DEVICES AND APPARATUS AND METHODS FOR MAKING AND DELIVERING THEM

RELATED APPLICATION DATA

This application is a continuation of co-pending International Application No. PCT/US2014/033892, filed Apr. 12, 2014, which claims benefit of U.S. provisional application Ser. Nos. 61/811,719 and 61/811,733, both filed Apr. 13, 2013. This application is also related to U.S. application Ser. No. 13/607,783, filed Sep. 9, 2013, International Application No. PCT/US2011/027726, filed Mar. 9, 2012, and provisional application Ser. Nos. 61/312,183, filed Mar. 9, 2010, and 61/385,483, filed Sep. 22, 2010. The entire disclosures of these applications are expressly incorporated by reference herein.

STATEMENT REGARDING FEDERALLY SPONSORED RESEARCH AND DEVELOPMENT

This invention was made with Government support under SBIR Grant Nos. 1143198 and 1329172 awarded by the National Science Foundation. The Government has certain rights in the invention.

FIELD OF THE INVENTION

The field of the invention generally relates to self-closing devices that are implantable within a patient's body and to apparatus, systems, and methods including such self-closing devices. For example, the present invention may include self-closing tubular structures, cuffs, or patches, and/or grafts that include resealable access ports or regions including self-closing tubular structures, and/or may include systems and methods for making and implanting such self-closing structures and/or grafts.

BACKGROUND

Dialysis for end stage renal disease ("ESRD") is one of the leading and rapidly growing problems facing the world today. In 2006, there were greater than fifty one million (51,000,000) people in the United States diagnosed with chronic kidney disease. Greater than five hundred thousand (500,000) people in this population suffered from ESRD. With the growing aging population and increasing prevalence of high risk factors such as diabetes (35% of all ESRD patients, Szycher M., *J Biomater Appl.* 1999; 13, 297-350) and hypertension (30%), the projected population in 2020 is greater than seven hundred eighty four thousand (784,000) (est. USRDS 2008).

The two primary modes of treatment are kidney transplant and hemodialysis. Due to the shortage of available transplant kidneys, approximately seventy percent (70%) of people with ESRD undergo hemodialysis (USRDS 2008) for life or until a transplant kidney becomes available. To facilitate the frequent, periodic treatments, patients must undergo vascular surgery to prepare their artery and vein, typically in their forearms, for dialysis. The two most common methods of preparing the artery and vein are arteriovenous (AV) fistulas and AV grafts—the former is the preferred option due to longer patency rates; however fistulas are often replaced by AV grafts once the life of the fistula has been exhausted.

There are advantages and disadvantages to both methods. Most notably, grafts are easy to implant, and ready to use relatively sooner, but have shorter lifespans and are more prone to infection and thrombus formation. Fistulas have greater durability and are less prone to infection, but can take up to six (6) months (KDOQI) to mature before use, and the veins used for access have tendencies to develop pseudo-aneurysms at the site of repeated access. One of the contributing factors to the rapid degradation of current AV grafts and/or veins is the repeated needle sticks during dialysis with relatively large needles (e.g., 14-16 Gauge). This is exacerbated because the average patient undergoes hemodialysis treatment two or three times a week, every week of every year until a kidney replacement is available or until the end of their life expectancy, which is approximately ten (10) years (Szycher M., *J Biomater Appl.* 1999; 13, 297-350). Moreover, due to the high risk of intimal hyperplasia and vessel narrowing, dialysis patients also undergo periodic interventional treatment to maintain patent vessels, which may occur several times a year. This typically involves angioplasty or stenting, akin to the treatment of coronary vascular occlusions, and vascular access using needles is also needed for these procedures, thereby contributing to the risk of graft or vessel degradation.

Therefore, there is an apparent need for devices, systems, and methods for treating ESRD and other conditions.

SUMMARY

The present application generally relates to self-closing devices that are implantable within a patient's body and to apparatus, systems, and methods including such self-closing devices. For example, apparatus, systems, and methods described herein may include self-closing tubular structures, cuffs, or patches, and/or grafts that include resealable access ports or regions including self-closing structures. In addition, systems and methods for making and using such devices are also provided.

In accordance an exemplary embodiment, a self-sealing access device is provided that includes base material, e.g., elastomeric and/or bioabsorbable material, including a surface area for securing the base material to a tissue structure; and a plurality of elastic support elements surrounding or embedded in the base material. The support elements may be separable to accommodate creating an opening through the base material for receiving one or more instruments through the base material, and biased to return towards a relaxed state for self-closing the opening after removing the one or more instruments. In exemplary embodiments, the device may be a cuff, a patch, or other device that may be secured around or to a tubular, curved, or substantially flat body structure.

For example, the support elements may include a plurality of struts spaced apart from one another to define openings in a relaxed or relatively low stress state. The struts may be separable from one another, e.g., to a relatively high stress state, to accommodate receiving one or more instruments through the openings and the base material filling or adjacent to the openings, the struts resiliently biased to return towards one another, e.g., to the relaxed or relatively low stress state.

In accordance with still another embodiment, a method is provided for implanting an access device into a patient's body that includes exposing a tubular body or other surface within a patient's body, e.g., a curved or substantially flat surface of a tubular body or other tissue structure, such as a vessel or graft, a heart, or a wall of the abdomen; and attaching an access device to the outer surface of the tubular body or tissue structure. The access device may include base material and a plurality of elastic support elements, the support elements separable to accommodate creating an opening through the base material for receiving one or more instruments through the base material, and biased to return towards a relaxed or relatively low stress state for self-closing the opening after removing the one or more instruments.

In accordance with yet another embodiment, a system is provided for accessing a tissue structure or graft implanted within a patient's body that includes a self-closing access device and an apparatus for introducing the access device into a patient's body. For example, the access device may include a cuff or patch that may be attached to the tissue structure or graft, e.g., including base material, e.g., elastomeric and/or bioabsorbable material, and a plurality of elastic support elements surrounding or embedded in the base material. The apparatus may include a dissector, e.g., having a blunt dissecting edge, carrying the access device, and a constraint for releasably securing the access device to the dissector. In an exemplary embodiment, the dissector may have a generally "C" shaped cross-section, e.g., defining a longitudinal slot, allowing the dissector and the access device thereon to be advanced over and/or around a blood vessel or other body structure.

In accordance with another embodiment, a method is provided for making an access device that includes wrapping a strand circumferentially around a mandrel in a zigzag pattern to define a first annular ring; offsetting the strand and wrapping the strand around the mandrel in a zigzag pattern to define a second annular ring adjacent the first annular ring; removing the strand from the mandrel; separating the first and second annular rings from one another resulting in free ends on each of the first and second annular rings; attaching the free ends together to define first and second enclosed annular rings; and embedding the first and second enclosed annular rings within a flexible base material.

In accordance with still another embodiment, a method is provided for making an access device that includes creating a plurality of zigzag bands disposed adjacent one another and one or more flexible connectors extending between adjacent zigzag bands, the flexible connectors biased to an original curved shape; elastically lengthening and at least partially straightening the flexible connectors to a stressed state, thereby increasing spacing between the adjacent zigzag bands; embedding the zigzag bands within a base material with the flexible connectors in the stressed state; and releasing the zigzag bands whereupon the flexible connectors are biased to return towards original the curved shape, thereby pre-stressing the base material in a longitudinal direction.

In accordance with yet another embodiment, a method is provided for making an access device that includes forming a layer of flexible base material defining first and second outer surfaces and a thickness therebetween; forming one or more elongate support strands biased to a curvilinear shape; threading the one or more elongate support strands through the base material, alternately, between the first and second surfaces and along a length of the base material.

In accordance with yet another embodiment, a method is provided for making an access device that includes creating a plurality of zigzag bands; creating a first layer of flexible base material including a first surface comprising a plurality of features corresponding to the shape of the zigzag bands; placing the zigzag bands against the first surface such that the zigzag bands are engaged with the features; and applying a second layer of flexible base material over the zigzag bands and the first layer.

In accordance with another embodiment, an access device is provided that includes a layer of flexible base material; a plurality of zigzag bands disposed adjacent one another, one or more flexible connectors extending between adjacent zigzag bands, the flexible connectors biased to an original curved shape and embedded within the base material after elastically lengthening and at least partially straightening the flexible connectors to a stressed state, the flexible connectors biased to return towards original the curved shape, thereby pre-stressing the base material in a longitudinal direction.

In accordance with still another embodiment, an access device is provided that includes a layer of flexible base material defining first and second outer surfaces and a thickness therebetween; and a plurality of elongate support strands biased to a curvilinear shape, the support strands threaded through the base material, alternately, between the first and second surfaces and along a length of the base material.

Other aspects and features of the present invention will become apparent from consideration of the following description taken in conjunction with the accompanying drawings.

BRIEF DESCRIPTION OF THE DRAWINGS

The drawings illustrate exemplary embodiments, in which:

FIG. 1A is a side view of a silicone sleeve including a plurality of rings including separable struts embedded therein.

FIG. 1B is a side view of the silicone sleeve of FIG. 1A split along a length of the sleeve.

FIGS. 2A-2C are top, bottom, and end views, respectively, of the sleeve of FIG. 1B covered with fabric to provide a cuff defining an integral penetrable, self-sealing access device.

FIGS. 11A and 1 1B are end and cross-sectional views, respectively, of a cylindrical mold including a cavity within which a set of elastic elements have been mounted for making a generally cylindrical access device.

FIGS. 12A-12D show exemplary methods for making a substantially planar access device including a plurality of elastic elements embedded in base material.

DETAILED DESCRIPTION OF THE EXEMPLARY EMBODIMENTS

Figure 3:
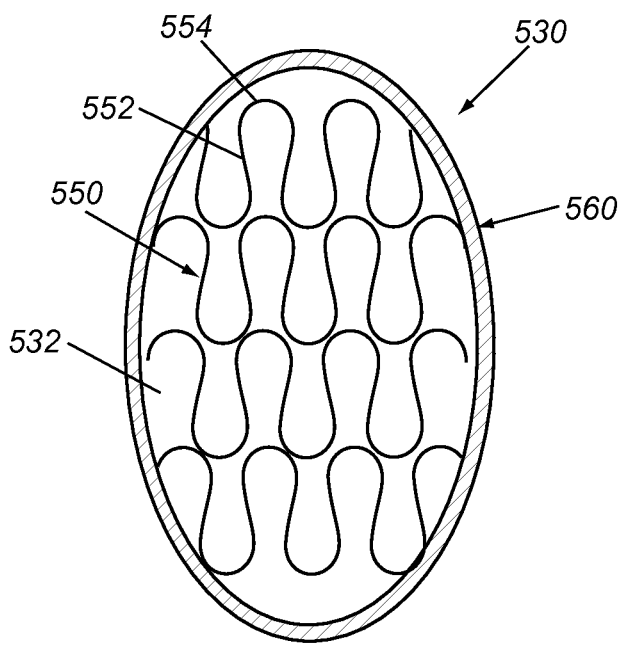
FIG. 3 is a top view of an exemplary embodiment of a reinforced patch including elastic support elements embedded in a base material and surrounded by a sewing ring.

Turning to the drawings, FIGS. 1A-2B show an exemplary embodiment of a self-sealing access device 330 in the form of a cuff including a generally annular port body 332 of flexible base material defining a central longitudinal axis 334, a plurality of bands 350 surrounding or embedded within the port body 332 (FIGS. 1A-1B), and fabric 360 covering exposed surfaces of the post body 332 (FIGS. 2A-2B). The port body 332 has a generally "C" shaped cross-section including longitudinal edges 336 extending between first and second ends 332a, 332b. Alternatively, the port body 332 may be provided as a patch or other body, e.g., including a substantially planar or curved surface that may be attached to a tissue structure or other body structure, as described elsewhere herein and in the applications incorporated by reference herein.

Figure 18:
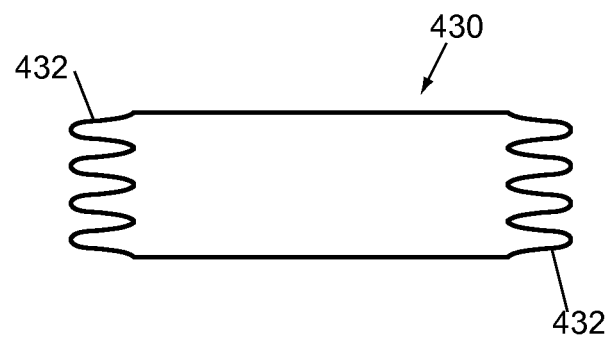
FIG. 18 is a side view of an exemplary embodiment of a generally cylindrical access device including a plurality of fingers on ends of the access device.

Optionally, the access device may include one or more additional features, e.g., to provide a transition between the access device and an underlying tubular structure to which the access device is secured. For example, FIG. 18 shows an exemplary embodiment of an access device 430, e.g., a cuff or sleeve including elastic elements (not shown) embedded therein, similar to any of the embodiments described elsewhere herein. The access device 430 includes fingers 432 extending from opposite ends of the elastomeric material, e.g., to provide greater flexibility, higher compliances, and/or prevent kinking of the ends when the access device is implanted on a body structure (not shown).

The port body 332 may be formed from one or more layers of flexible base material, e.g., silicone, polyurethane, or other elastomeric or nonporous and/or flexible material. In addition or alternatively, the port body 332 may be formed from bioabsorbable material, e.g., polyethylene glycol, PLA, PGA, small intestinal submucosa (SIS), and the like, as described further in the applications incorporated by reference herein.

The bands 350 may be formed from continuous rings or "C" shaped collars of Nitinol or other elastic, superelastic, or shape memory material formed, e.g., laser cut, mechanically cut, stamped, machined, and the like, from a tube, wire, or sheet, e.g., similar to embodiments described in the applications incorporated by reference herein. Each band 350 may extend at least partially around the periphery of the port body 332 transverse to the longitudinal axis 334. For example, each band 350 may include a plurality of longitudinal struts 352 extending including opposing ends that are alternately connected to adjacent struts 352 by curved circumferential connectors, struts, or elements 354, e.g., to define a zigzag or other serpentine pattern. The longitudinal struts 352 may extend substantially parallel to the longitudinal axis 334 or, alternatively, may extend diagonally or helically relative to the longitudinal axis 334 (not shown).

Alternatively, the access device 330 may include a contiguous mesh or other enclosed or open pattern including struts at least partially surrounding openings (not shown) through which one or more instruments may be inserted, as described further elsewhere herein. For example, individual bands or a substantially continuous mesh sheet may be provided that include interconnected struts defining generally diamond-shaped or other enclosed openings therebetween (not shown), with the struts being separable to increase the size of the openings, e.g., to accommodate receiving one or more instruments therethrough, as described elsewhere herein. Exemplary mesh patterns that may be used are shown in U.S. Pat. Nos. 4,733,665, 5,344, 426, and 5,591,197 the entire disclosures of which are expressly incorporated by reference herein. In further alternatives, the access device 330 may include one or more wires or other elongate filaments wound helically or otherwise around the port body 332 and/or along a desired length of the port body 332, e.g., a single helical element, multiple helical filaments braided or otherwise wound together into a mesh, and the like.

In a further alternative, struts or bands may extend axially along a length of the access device 330 (not shown). For example, a plurality of substantially straight wires or other filaments may be embedded within or otherwise fixed to the base material. The filaments may be spaced apart sufficiently to accommodate inserting one or more instruments (not shown) through the access device 330, with the filaments moving laterally to accommodate the instrument(s) passing therethrough and resiliently returning to their original configuration to substantially seal the access device 330, similar to other embodiments herein. Alternatively, the filaments may include a zigzag or other pattern that extends transversely while the filaments extend generally axially between the ends of the access device 330, e.g., similar to the embodiment shown in FIG. 17C and described further elsewhere herein. Further, the filaments or struts may impose a substantially continuous compressive force on the adjacent base material, which may enhance sealing any passages created through the base material, also similar to other embodiments herein and in the applications incorporated by reference herein.

The struts, filaments, or features of the bands or mesh, e.g., the struts 352 and curved connectors 354 shown in FIGS. 1A and 1B, may have any desired cross-section. For example, the features may have generally round, elliptical, rectangular, or square cross-sections, optionally, having tapered or rounded surfaces to facilitate passing an instrument between the features. For example, the features may be formed with a rectangular cross-section that may have rounded or tapered edges, e.g., by one or more of electro-polishing, machining, laser cutting, and the like. Optionally, the features may have a thickness (extending radially relative to the central longitudinal axis 334) that is greater than their width (extending axially and/or circumferentially), which may provide increased radial support yet accommodate separation of the features "laterally," as described further elsewhere herein.

In the embodiment shown in FIGS. 1A and 1B, each band 350 has a generally cylindrical shape, e.g., including first and second longitudinal ends that are spaced apart axially from one another and aligned around the periphery of the port body 332, e.g., substantially perpendicular to the longitudinal axis 334. Alternatively, the bands 350 may extend helically around the periphery of the port body 332 (not shown) and/or may have other shapes or configurations including an axial length dimension along a length of the port body 332 and a peripheral dimension extending at least partially around the periphery of the port body 332.

The bands 350 may be disposed immediately adjacent one another, e.g., with adjacent bands 350 in phase with one another. For example, as shown in FIGS. 1A and 1B, the curved connectors 354 on the first end of a first band 350 may be disposed between the curved connectors 354 on the second end of an adjacent band 350, e.g., to partially nest adjacent bands 350. Alternatively, adjacent bands 350 may be spaced axially apart from one another (not shown), thereby providing an unreinforced annulus of the port body 332 between adjacent bands 350, which may accommodate introducing relatively large instruments between the struts 352 and/or bands 350, as described further below. In another alternative, portions of adjacent bands may overlap one another (not shown) or a braided or other multiple layer mesh may be provided (also not shown), as long as struts or other elements of the mesh are free to move laterally and/or resiliently to accommodate one or more instruments through openings between the elements. Optionally, in these embodiments, adjacent bands 350 may be connected to one another by one or more links or connectors, e.g., similar to those shown in FIGS. 8-9B and described elsewhere herein.

In a further alternative, adjacent bands 350 may be out of phase with one another, e.g., such that the curved connectors 354 of adjacent bands 350 are disposed adjacent one another, e.g., aligned axially or diagonally relative to one another (not shown). In this alternative, adjacent bands may define openings surrounded by pairs of struts from each adjacent band, which may accommodate receiving relatively large instruments through the openings yet substantially closing the openings once the instrument(s) are removed. Optionally, in this alternative, one or more of the curved connectors 354 on a band 350 may be coupled to one or more curved connectors 354 of an adjacent band 350. For example, adjacent curved connectors 354 may be coupled directly together, or may be coupled by a flexible link or connector (not shown), e.g., to limit movement of adjacent bands 350 relative to one another.

Alternatively, composite and/or variable materials may be used for the base material and/or elastic elements to provide varying compliance at desired locations of the port body 332. For example, the base material and/or elastic elements may be configured such that ends or peripheral edges of the resulting access device are more compliant and/or the compliance varies along the length of the device. For example, the struts of the elastic elements may be thinner and/or the base material may have a narrower thickness at the ends. Such varying compliance may improve the ability of the resulting access device to accommodate nonlinear and/or tortuous anatomy.

Turning to FIG. 1A, the access device 330 may be formed by initially creating a tubular body or sheet of silicone, PET, or other flexible, nonporous, and/or bioabsorbable base material having a desired length and/or diameter for the port body 352, e.g., by one or more of molding, casting, machining, spraying, spinning, deposition, and the like, as described elsewhere herein. For example, the tubular body may have a length between about one and ten centimeters (1-10 cm), a diameter between about one and forty millimeters (1-40 mm), and a wall thickness between about 0.5 and five millimeters (0.5-5.0 mm).

Figure 7A:
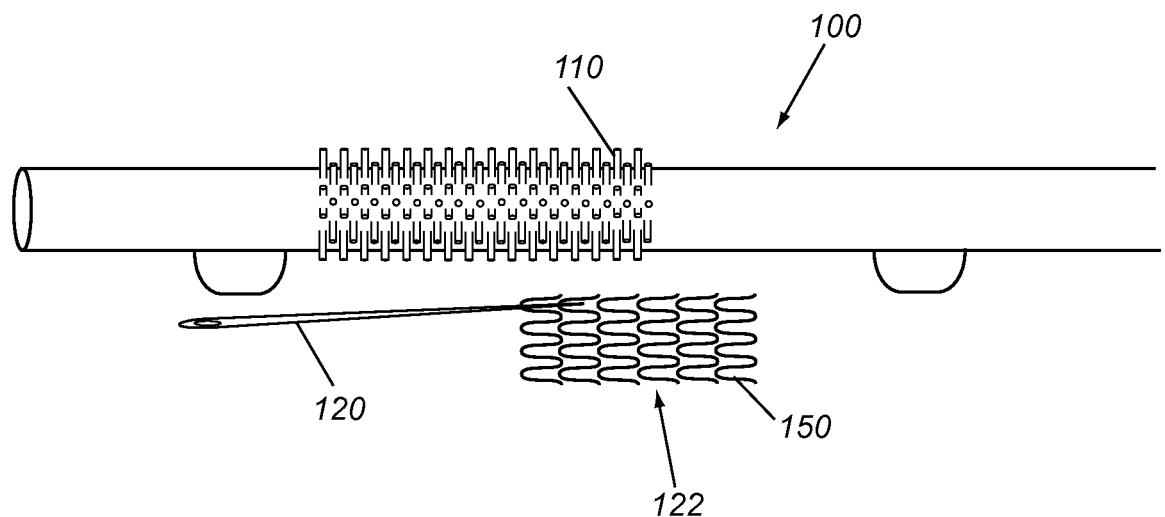
FIG. 7A is a side view of an exemplary apparatus for making a plurality of rings that may be embedded within base material to provide an access device, such as that shown in FIGS. 2A-2C.
Figure 7B:
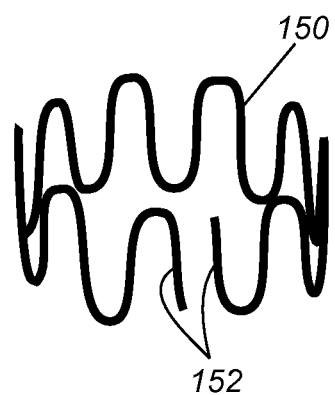
FIGS. 7B and 7C are perspective and side views, respectively, of an exemplary ring that may be formed using the apparatus of FIG. 7A.
Figure 7C:
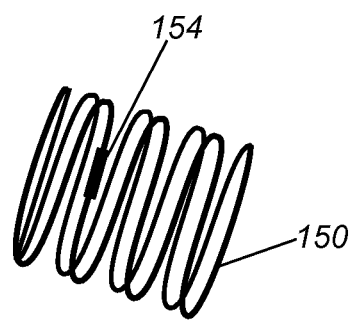

The set of bands 350 may be formed individually or simultaneously, e.g., by laser cutting from a tube, winding one or more strands in a zigzag or other circuitous pattern around a mandrel, and the like, e.g., as described elsewhere herein. For example, a length of Nitinol wire or other material 120 may be wound around a cylindrical mandrel 100 between pins 110 to define a zigzag or other circuitous pattern to define an enclosed band (or entire set of bands 122), e.g., as shown in FIGS. 7A-7C and described elsewhere herein, or may be wound helically along a mandrel to define a substantially continuous helical band (not shown). Alternatively, a single tube may be cut to create the set of bands 350 or a substantially continuous mesh of struts (not shown), as desired. The individual or set of bands 350 may have lengths between about three and one hundred twenty five millimeters (3.0-125 mm), e.g., coextensive with or less than the length of the port body 352.

Alternatively, the bands 350 may be formed from a flat sheet, e.g., by one or more of laser cutting, mechanically cutting, etching, stamping, and the like, to provide one or more sets of struts and connectors from the sheet, and then rolling the sheet. The longitudinal edges of the rolled sheet may remain separate, e.g., to provide "C" shaped bands, or alternatively the longitudinal edges may be attached together, e.g., by one or more of welding, soldering, fusing, bonding with adhesive, using connectors (not shown), and the like, to provide an enclosed band. In a further alternative, a set of bands 350, e.g., providing an entire set for the access device 330, may be formed simultaneously from a tube or sheet, particularly if the bands 350 are connected together, e.g., by links or directly by adjacent connectors 354.

The bands 350 may be heat treated and/or otherwise processed to provide a desired finish and/or mechanical properties to the bands 350. For example, the bands 350 may be heat treated such that the bands 350 are biased to a desired relaxed diameter, e.g., substantially the same as or smaller than the tubular body for the port body 332, yet may be resiliently expanded and/or have one or more struts 352 and/or curved connectors 354 resiliently deformed to accommodate receiving a needle or other instrument (not shown) between adjacent struts 352, connectors 354, and/or bands 350, as described further below. Alternatively, if the bands 350 are formed from a sheet of material, the sheet may be heat treated and/or otherwise processed to provide the desired shape and/or properties for the bands 350 formed from the sheet.

In an exemplary embodiment, for Nitinol material, the bands 350 may be heat treated such that the $A_f$ temperature for the material is less than body temperature (about 37° C.), e.g., between about ten and thirty degrees Celsius (10-30° C.). For example, the Nitinol material may remain substantially in an Austenitic state when the access device 330 is implanted within a patient's body, yet may operate within a superelastic range, e.g., transforming to a stress-induced martensitic state when an instrument is inserted through the openings in the access device 330, as described elsewhere herein. Alternatively, the Nitinol material may be heat treated to take advantage of the temperature-activated or other shape memory properties of the material. For example, the material may be heat treated such that the bands 350 are substantially martensitic at or below ambient temperature, e.g., below twenty degrees Celsius (20° C.), such that the bands 350 may be relatively soft and/or plastically deformable, which may facilitate manipulation, introduction, or implantation of the access device 330. At around body temperature, e.g., at thirty seven degrees Celsius (37° C.) or higher, the bands 350 may be substantially austenitic, e.g., to recover any desired shape programmed into the material and to provide elastic or superelastic properties to the bands 350 once the access device 330 is implanted within a patient's body.

With continued reference to FIG. 1A, to form the access device 330, a set of bands 350 may be fixed to, e.g., placed on, bonded to, or embedded in, the tubular body or other base material of the port body 332, e.g., as described elsewhere herein. For example, in their relaxed state, the bands 350 may have a diameter smaller than the base material of the port body 332, and the bands 350 may be expanded radially outwardly, positioned around the tubular body, and released such that the bands 350 apply a radially inward compressive force against the tubular body. Such compression may be sufficient to bias the port body 332 to a desired diameter, e.g., smaller than a tubular body to which the access device 330 may be secured, for example, to reduce migration and/or otherwise secure the access device 330. In addition, such compression may impose a substantially continuous compressive force on the port body 332, which may enhance the self-sealing function of the access device 330. Alternatively, the bands 350 may be biased to a diameter similar to the outer surface of the tubular body such that the bands 350 surround the tubular body without substantial radially inward compression. In this alternative, the bands 350 may remain in a substantially relaxed state and/or may not apply a radially inward compressive force against the base material of the port body 332

Optionally, the bands 350 may be expanded "laterally" in addition to or instead of being radially expanded. For example, the bands 350 may be expanded radially from a relaxed state to increase the spacing of the struts or filaments, i.e., increase the size of the openings defined by the bands 350, and then placed on, embedded in, and/or otherwise attached to the base material of the port body 332. In this embodiment, once the bands 350 are fixed to the port body 332, the bands 350 may be released such that the bands 350 are biased to return laterally inwardly towards the relaxed state, thereby biasing the struts and openings to a smaller size, yet accommodating the struts moving laterally to accommodate an instrument being inserted through the openings, as described elsewhere herein.

As described above, once fixed to the port body 332, the bands 350 may be spaced apart from, may contact, may overlap, or may be nested between adjacent bands 350, e.g., in phase or out of phase with one another, as desired. Alternatively, if the bands 350 are connected to one another, the entire set of bands 350 may be positioned around the tubular body with or without expanding and releasing the bands.

Figure 14A:
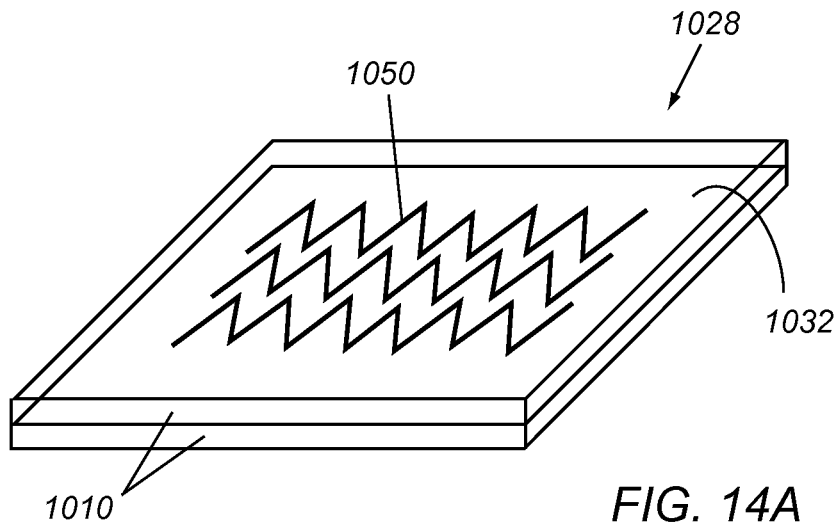
FIGS. 14A-14C show another exemplary method for making an access device including a plurality of layers of base material thermally welded around a set of elastic elements.
Figure 14B:
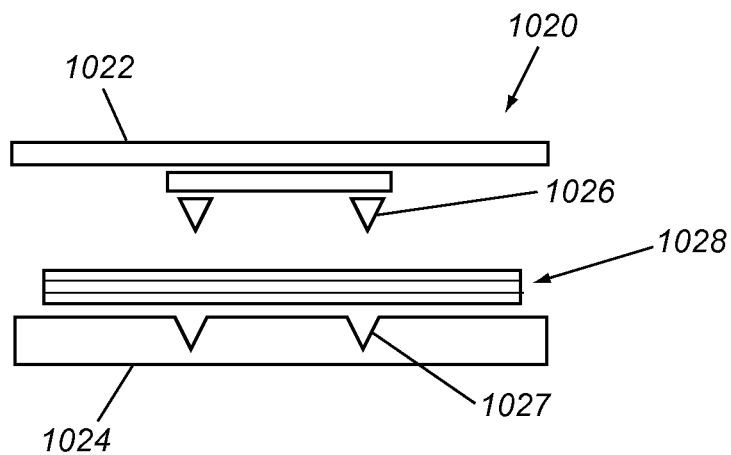
Figure 14C:
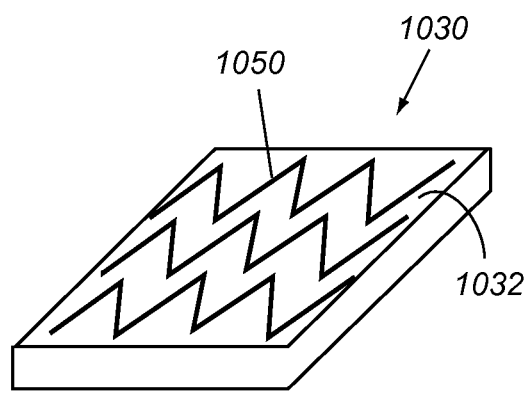

Optionally, with the bands 350 surrounding, placed against, and/or fixed relative to the base material of the port body 332, another layer of silicone, PET, or other flexible base material may be applied around the bands 350 to further form the port body 332, thereby embedding the bands 350 within the base material. For example, an outer layer of silicone may be applied around the bands 350 and the assembly may be heated, cured, or otherwise processed to fuse, melt, or otherwise bond the material of the outer layer to the bands 350 and/or the material of the tubular body, e.g., as shown in FIGS. 14A-14C and described elsewhere herein. Alternatively, the tubular body may be softened or otherwise treated to allow the bands 350 to become embedded therein, or the tubular body may be formed around the bands 350, if desired. In a further alternative, the bands 350 may be secured around the tubular body, e.g., by one or more of bonding with adhesive, sonic welding, fusing, and the like.

As shown in FIGS. 1A and 1B, a plurality of bands 350 are embedded in or secured around the port body 332, e.g., two, three, four, five (as shown), or more bands 350, as desired. For example, as shown, the bands 350 may be provided along substantially the entire length of the port body 332. Alternatively, the bands 350 may be provided only in a central region of the port body 332, e.g., with regions adjacent the first and second ends 332a, 332b including unsupported silicone or other base material (not shown) and/or fingers or other transition features, such as the fingers 432 shown in FIG. 18.

Returning to FIGS. 1A and 1B, once the bands 350 are embedded within or otherwise secured to the port body 332, the port body 332 may be split or otherwise separated, e.g., by one or more of laser cutting, mechanical cutting, and the like, through the silicone material and the bands 350, to provide the side edges 336, as shown in FIG. 1B. Alternatively, the bands 350 may be formed as discontinuous "C" shaped collars that may be attached around or embedded within the port body 332 before or after splitting the port body 332 to create the longitudinal edges 336. In a further alternative, a length of base material with embedded bands corresponding to multiple individual access devices may be formed using the methods described above, and the resulting assembly may be cut or otherwise separated into individual port bodies 332, if desired. In yet a further alternative, the bands and port bodies may not be cut longitudinally, if a tubular access device is desired, similar to other embodiments herein.

Turning to FIGS. 2A-2C, fabric 360 may be applied over any exposed surfaces, e.g., over the outer, inner, and end surfaces of the port body 332 to provide the completed access device 330. For example, one or more pieces of fabric 160 may be wrapped around the port body 332 and stitched together and/or to the port body 332, e.g., similar to embodiments in the applications incorporated by reference herein. Optionally, the access device 330 may include one or more tactile elements, ferromagnetic elements, echogenic elements, and the like (not shown), e.g., to facilitate locating the access device 330 and/or bands 350 when the access device 330 is implanted subcutaneously or otherwise within a patient's body, such as those disclosed in the applications incorporated by reference herein.

During use, the access device 330 may be positioned around a tubular structure, e.g., a graft before or after implantation, a blood vessel, fistula, or other tubular structure (not shown) exposed or otherwise accessed within a patient's body. For example, the side edges 336 may be separated, and the port body 332 positioned around or otherwise adjacent a tubular structure. The side edges 336 may be released to allow the port body 332 to resiliently wrap at least partially around the tubular structure and/or the port body 332 may be attached to the tubular structure, e.g., by one or more of bonding with adhesive, suturing, fusing, and the like. Alternatively, if the access device includes an enclosed tubular port body (not shown), the access device may be directed over a tubular structure from one end thereof (which may be preexisting or may be created by cutting the tubular structure).

In an alternative embodiment, an access device similar to access device 330 may be attached to a tubular graft or other structure before introduction and/or implantation within a patient's body. In another alternative, the access device 330 may be integrally formed into the wall of a graft, e.g., during manufacturing of the graft, if desired. For example, rather than providing a separate port body 332, the bands 350 or other support elements may be integrally molded or otherwise embedded within a wall of a tubular graft or other implant. Thus, the implant may include an integral access device that operates similar to the other embodiments herein.

Returning to FIGS. 2A-2C and with reference to the access device 330, if it is desired to access a lumen of the tubular structure, a needle (not shown) may be introduced through the patient's skin over the access device 330, and directed through the port body 332 into the lumen. The thickness of the access device 330 may facilitate identifying the ends of the access device 330, e.g., by palpation, since the ends may be identified tactilely relative to the adjacent regions of the tubular structure. Thus, the access device 330 may reduce the risk of accidental sticks in regions of the tubular structure not covered by the access device 330.

As the needle is inserted, if the needle encounters any of the struts 352, connectors 354, or other features of the bands 350, the encountered features may resiliently move away from the needle to create a passage through the access device 330 into the lumen. If one or more larger instruments are subsequently introduced through the access device 330, e.g., over a guidewire advanced through the needle or over the needle itself, the struts 352, connectors 354, and/or other features of the bands 350 may resiliently separate to create a sufficiently large passage through the port body 332 to accommodate the instrument(s). Generally, the struts 352, connectors 354, and/or other features of the bands 350 separate "laterally," i.e., circumferentially and/or axially within the cylindrical surface defined by the port body 332, to provide a passage through the port body 332. As used herein, "laterally" refers to movement of the features of the bands 350 or other mesh substantially in a direction around the circumference and/or along the length of the port body 332 within the base material and generally not out towards the inner or outer surfaces of the port body 332 (i.e., "within the plane" of the port body 332). For example, if the port body 332 were substantially flat within a plane, laterally would refer to movement of the features of the bands substantially within the plane and generally not out of the plane towards the inner or outer surfaces.

After a procedure is completed via the access device 330 and the lumen of the tubular structure, any instruments may be removed, whereupon the bands 350 may resiliently return towards their original shape, e.g., laterally inwardly towards their original configuration, thereby compressing the base material of the port body 332 to close any passage created therethrough. Thus, the bands 350 may provide a self-sealing or self-closing feature that automatically substantially seals any passages created through the port body 332 by a needle or other instruments.

For example, if the spacing of the struts or other features of the bands 350 is smaller than the cross-section of the instrument(s) inserted through the access device 330, the features may separate to create a passage through the access device 330 that is larger than the spacing of the features in their relaxed state. However, even if the spacing of the features is larger than the cross-section of the instrument(s) inserted through the access device 330, the bands 350 may provide sufficient bias within the plane of the port body 332 to bias the port body material to resiliently close laterally inwardly around any passage created therethrough to automatically close the passage. Thus, the elasticity/bias of the bands 350 may reinforce and/or bias the material of the port body 332 to allow repeated access through the access device 330, while automatically closing any passages to self-seal the access device 330. The bias or support of the port body material between the struts of the bands 350 may also reduce the risk of the material breaking down over time due to multiple penetrations.

One of the advantages of the access device 330 is that a needle or other instrument may be introduced at multiple locations through the port body 332. As long as the needle is inserted through a region of the access device 330 including and/or supported by one or more bands 350, the features of the bands 350 may separate or otherwise open to accommodate the needle and resiliently return towards their substantially stress free or preloaded original configurations when all instruments are removed.

In addition, such bands 350 may protect the accessed tubular structure from over-penetration of needles or other instruments. For example, if the access device 330 substantially surrounds the tubular structure, a needle or other instrument that is inadvertently inserted into one side of the access device 330 through the entire tubular structure and out the opposite side of the access device 330 may be removed without substantial risk of bleeding or other leakage from the posterior location as well as the anterior location since the access device 330 may self-seal both openings.

Optionally, if the port body 332 has a periphery defining less than one hundred eighty degrees (180°) or is substantially flat, the access device 330 may be applied as a patch to the surface of any body structure, e.g., a tubular structure, such as a graft, fistula, blood vessel, and the like, or to an organ, abdominal wall, or other tissue structure. The "patch" may have a variety of shapes and/or sizes depending upon the application and/or may have sufficient flexibility to conform to the shape of anatomy to which the patch is applied. For example, the port body 332 may have a two-dimensional shape, e.g., a rectangular, square, oval, or circular shape, with bands 350 provided along the entire surface area of the port body 332 or spaced apart inwardly from an outer perimeter of the "patch." Such patches may be created by cutting or otherwise separating a desired shape from the tubular body described above after embedding or securing bands thereto. Alternatively, individual patches may be created by embedding or securing flat bands to patches of silicone or other base material formed into the desired shape.

In a further alternative, the patch may be created by laminating multiple layers of material to create a self-sealing structure that may be attached to a tissue structure. For example, each layer may include elastic support elements, e.g., a mesh, struts, and the like, that support one or more layers of base material within a plane of the base material(s). Alternatively, one or more layers of base material may be provided that has sufficient flexibility and bias such that the support elements may be omitted.

The resulting patch may accommodate creating an opening through the base material(s) of the layers when one or more instruments are inserted through the patch, i.e., with the support elements moving laterally within the plane of the base material(s). After removing the instrument(s), the support elements may bias the base material(s) of the respective layers laterally towards their original configuration, thereby automatically closing the opening.

Alternatively, the access device 330 may be provided in a three-dimension configuration, e.g., a conical, parabolic, or other shape (not shown). In addition or alternatively, the access device 330 may be provided in a curved cylindrical (e.g., substantially uniform or tapered) or other shape having a desired arc length, e.g., up to sixty degrees (60°), one hundred twenty degrees (120°), between five and three hundred sixty degrees (5-360°), between one hundred eighty and three hundred sixty degrees (180-360°), and the like. The port body 332 may be biased to a predetermined three-dimensional shape yet sufficiently flexible to accommodate the actual anatomy encountered, e.g., having one or more bands or other structures including elastic struts embedded within or otherwise secured to a flexible base material, such as silicone, polyurethane, or other elastomer, similar to other embodiments herein.

Optionally, the access device 330 may be used as a patch or surgical mesh, e.g., which may be attached or otherwise secured to weakened areas of tissue or organs to provide reinforcement in addition to allowing subsequent access, if desired. For example, the access device 330 may be applied as a patch for vascular repair, e.g., over a pseudo-aneurysm, or after excising a pseudo-aneurysm to reinforce the region and/or allow subsequent access.

Turning to FIG. 3, an exemplary embodiment of a surgical patch 530 is shown that includes one or more layers of base material 532, e.g., defining a substantially flat or curved "plane," and a plurality of support elements or bands 550 embedded or otherwise attached to the base material 530. For example, the base material 532 may include one or more layers of silicone or other elastomeric material that may be biased to a flat or curved planar shape or may be "floppy," i.e., may have no particular shape and may conform substantially to any desired shape. As shown, the support elements include a plurality of bands 550 including features, e.g., struts 552 alternately connected by curved connectors 554, similar to other embodiments herein. The bands 550 may extend along a substantially linear axis across the base material 532, e.g., defining a sinusoidal or other alternating pattern, adjacent to and substantially parallel to one another. Thus, the features, e.g., struts 552 and connectors 554, may support the base material 532, such that the support elements 550 may be separable laterally to accommodate receiving one or more instruments (not shown) through the base material 532, yet resiliently biased to close any openings through the base material 532 created by the instrument(s), similar to other embodiments herein.

Alternatively, the patch 530 may include one or more layers of base material 532 without the support elements 550 covered with fabric or other material (not shown). The base material 532 may be constructed to be self-supporting and resiliently biased to allow the creation of passages therethrough by a needle or other instrument (not shown), yet self-close the passage(s) upon removal of the instrument(s) to prevent substantial leakage through the patch 530. For example, each layer of base material may provide axial strength in a desired axial direction, and multiple layers may be attached together with the axial directions orthogonal or otherwise intersecting one another. The direction of axial strength may be achieved by selection of the polymer or other material for the base material or by embedding strands, wires, or other axial elements within the base material (not shown). Similar to other embodiments herein the patch 530 may be biased to a substantially flat configuration, a curved configuration, or may be "floppy," as described elsewhere herein.

In addition, as shown in FIG. 3, the surgical patch 530 may include a sewing ring or cuff 560 extending around a periphery of the base material 532, e.g., to facilitate securing the patch 530 to tissue, as described further below. For example, the sewing ring 560 may include one or more layers of fabric or other material, e.g., optionally filled with foam, fabric, or other resilient, flexible, and/or penetrable material, attached to the periphery of the base material 532, e.g., by stitching with sutures, bonding with adhesive, and the like. The base material 532 may also be covered with fabric or other material, e.g. the same or different material than the sewing ring 560, to enhance tissue ingrowth and/or integrate the components of the patch 530.

The patch 530 may have a generally round shape, e.g., an elliptical, oval, or substantially circular shape. Alternatively, the patch 530 may have a square or other rectangular shape, or other geometric shape, as desired.

In an alternative embodiment, the patch 530 may be provided in a "cut-to-length" configuration, e.g., an elongate sheet or roll (not shown) of base material 532, having a predetermined width and a length sufficient to provide multiple individual patches. In this alternative, the sewing ring 560 may be omitted or may be provided along the longitudinal edges of the sheet or roll. Optionally, the sheet or roll may include weakened regions to facilitate separating individual patches or may include unsupported regions without support elements 550 between regions with support elements 550, e.g., that may be easily cut otherwise separated to allow individual patches to be separated from the sheet or roll.

Figure 4A:
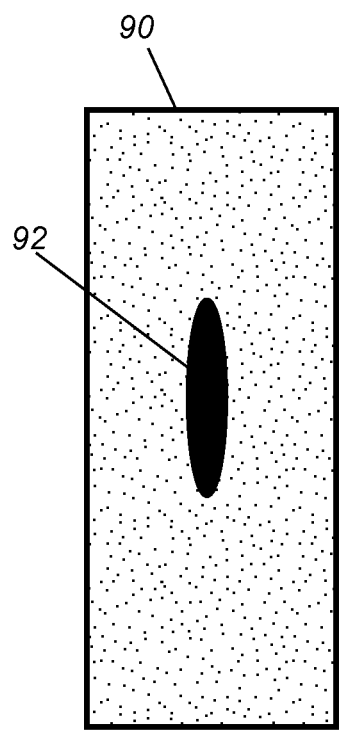
FIGS. 4A-4C are top views of a wall of a vessel, showing a method for repairing the wall using the patch of FIG. 3.
Figure 4B:
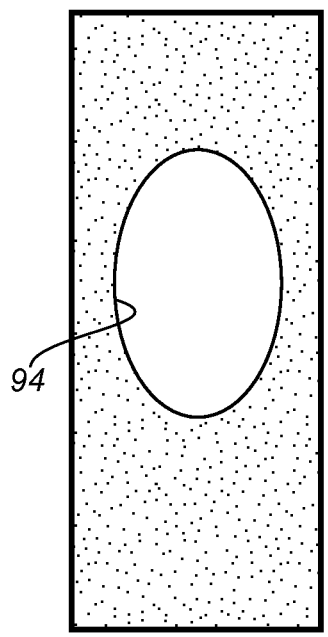
Figure 4C:
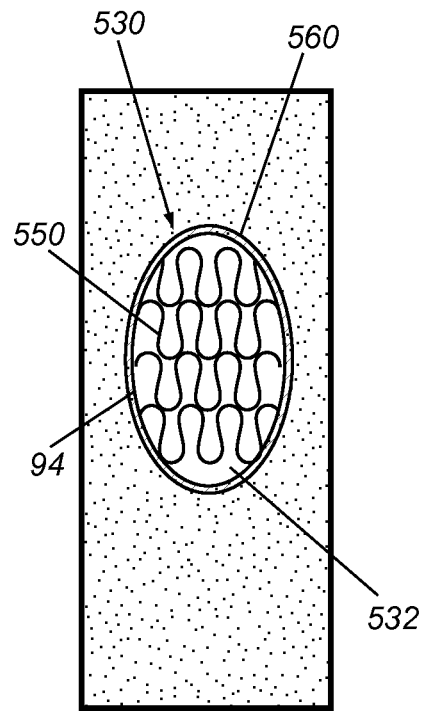

Turning to FIGS. 4A-4C, an exemplary method is shown for vascular repair using the patch 530 of FIG. 3. As shown in FIG. 4A, a blood vessel 90 may include a weakened region 92 in need of repair. Turning to FIG. 4B, the weakened region 92 and adjacent tissue may be resected to create an opening 94, e.g., corresponding to the size and shape of the patch 530. The patch 530 may then be attached within or over the opening 94, e.g., by suturing the sewing ring 560 to the vessel wall surrounding the opening 94. Alternatively, the patch 530 may be attached to the wall of the vessel 90 without removing the weakened region 92, e.g., by attaching the patch 530 to the vessel 90 over the weakened region 92 or within the lumen underlying the weakened region 92, thereby supporting the weakened region 92. In another alternative, the patch 530 may be attached to a vessel wall that does not include a weakened region, e.g., as a prophylactic measure to prevent a weakened region from developing at the site of implantation. The patch 530 may thereafter provide a structure for supporting the vessel wall and/or provide a self-closing structure allowing multiple access to the vessel 90, similar to other embodiments herein.

In another embodiment, an access port patch may be attached to the apex of the left ventricle of a heart to facilitate trans-apical procedures, e.g., aortic valve replacement, and the like. Such a patch may allow one-time or repeated access through the LV apex into the left ventricle. Once the procedure is completed, any instruments introduced through the patch may be removed, and the patch may provide substantially instantaneous sealing of the LV apex.

In another option, the access device 330 may be provided in a tubular or "C" shaped configuration, and may be introduced into a blood vessel or other body lumen. For example, the access device 330 may be rolled or otherwise compressed, and loaded into a catheter, delivery sheath, and the like (not shown). Alternatively, the access device 330 may be advanced over a needle, e.g., a dialysis needle, into the interior of a graft, fistula, or other tubular structure after dialysis. Once deployed within a lumen of a tubular structure or body lumen, the access device 330 may be attached to the wall of the body lumen, e.g., by one or more of stitching with sutures, bonding with adhesive, interference fit due to the radial bias of the access device 330, and the like. Thus, the access device 330 may provide an immediate barrier to leakage through a wall of the body lumen, e.g., to substantially seal a puncture site from the interior of the body lumen. In addition, the access device 330 may allow the lumen to be subsequently accessed again, as desired, with the access device 330 providing a self-sealing access region, similar to other embodiments herein.

Figure 5A:
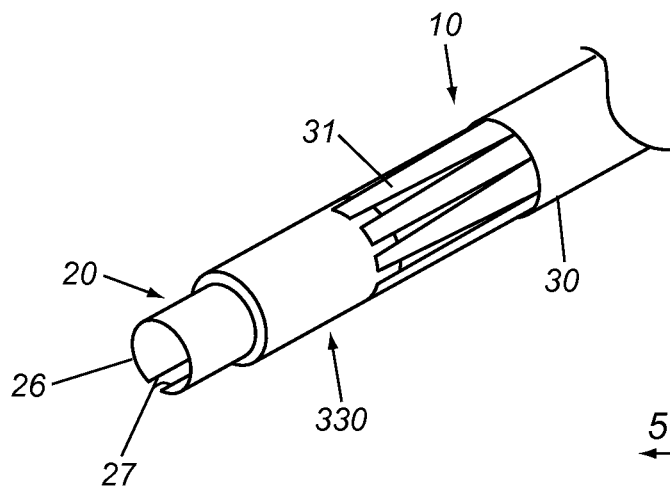
FIGS. 5A-5C are perspective, side, and end views, respectively, of an apparatus for delivering an access device, such as the cuff of FIGS. 2A-2C or the patch of FIG. 3.
Figure 5B:
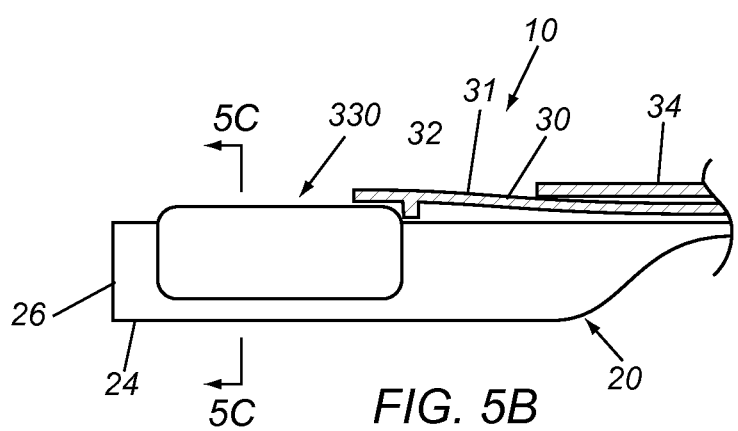
Figure 5C:
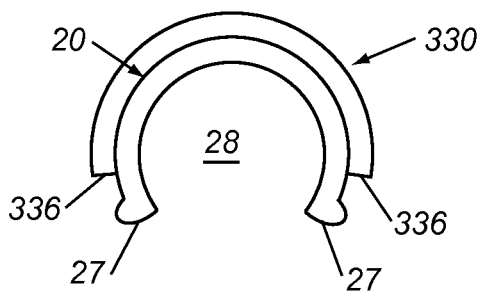

Turning to FIGS. 5A-5C, an exemplary embodiment of an apparatus 10 is shown for implanting an access device 330, e.g., a cuff or patch, such as those described elsewhere herein and in the references incorporated by reference herein. Generally, the apparatus 10 includes a dissector 20 carrying the access device 330 and a constraint 30 for releasably securing the access device 330 to the dissector 20.

The dissector 20 generally includes a proximal end, e.g., including a handle (not shown), and a distal end or portion 24 having a "C" shaped cross-section and including longitudinal edges 27 defining a slot, thereby defining a lumen or passage 28 therein for receiving a body structure, e.g., a blood vessel, fistula, tubular graft, and the like (not shown). In an exemplary embodiment, the distal end portion 24 of the dissector 20 terminates in a substantially atraumatic and/or blunt distal tip 26, e.g., to provide a blunt dissection edge, which may facilitate placement of the access device 330 on or around a body structure. For example, the blunt distal tip 26 may allow tissue or other material attached to or disposed adjacent the outer surface of the body structure to be removed, dissected, and/or otherwise directed away from the body structure, e.g., to provide a target implantation site for the access device 330. Alternatively, the distal tip 26 may include a sharpened or other edge to enhance dissection or cutting tissue, if desired.

The "C" shaped distal end portion 24 of the dissector 20 may have a length longer than the access device 330, e.g., such that the entire access device 330 may be supported and/or otherwise carried on the outer surface of the distal end 24. Proximally, the dissector 20 may transition to a shaft or other structure coupled to the handle and/or proximal end, e.g., to facilitate manipulation of the apparatus 10. Optionally, the handle or proximal end may include one or more markers (not shown) to identify the orientation of the distal end portion 24, e.g., to facilitate a user identifying the orientation of the longitudinal edges 27 and/or the location of the slot when the distal end portion 24 is introduced into a patient's body.

The distal end portion 24 may have sufficient column strength to be advanced or otherwise manipulated from the proximal end, yet may have sufficient flexibility to be introduced and/or positioned as desired, e.g., around a body structure within a patient's body. For example, the distal end portion 24 may be sufficiently flexible such that the longitudinal edges 27 may be separated to accommodate a body structure being received through the slot into the interior 28 of the dissector 20. In an exemplary embodiment, the distal end 24 portion may have a cross-section defining a portion of a circle or other arcuate shape, e.g., extending up to or greater than 180° around the periphery of the target body structure, having a diameter corresponding to the body structure such that the longitudinal edges 27 may resiliently separate and then wrap around and/or engage the body structure to dissect surrounding tissue.

Figure 6A:
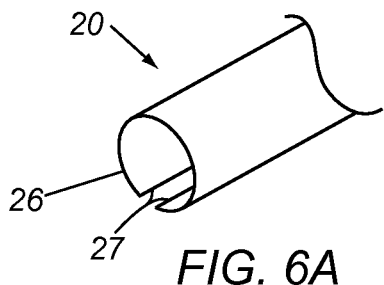
FIGS. 6A-6C are perspective views of alternative embodiments of a blunt dissector that may be included in the apparatus of FIGS. 5A-5C.
Figure 6B:
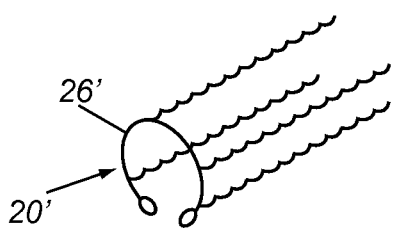
Figure 6C:
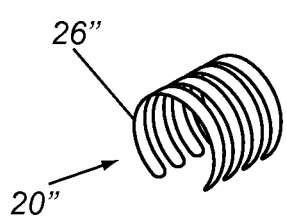

FIGS. 6A-6C show exemplary embodiments that may be provided for the distal end portion 24 of the dissector 20. For example, FIG. 6A shows a "C" shaped tube 20, e.g., a tubular structure that may have the slot formed therein, e.g., by cutting, molding, and the like, terminating in a substantially blunt distal tip 26. FIG. 6B shows a "C" collar defining the distal tip 26' and a plurality of spring elements extending proximally from the distal tip 26,' e.g., to carry the access device 330 and support the distal tip 26.' FIG. 6C shows a "C" shaped spring element 20," e.g., including a plurality of "C" shaped wires or other structures connected sequentially to one another along the distal end and terminating in a blunt distal tip 26." Such spring elements may provide flexibility to accommodate bending, e.g., during introduction of the dissector 20,' 20" while providing sufficient column strength or axial stiffness to allow dissection when advanced.

The constraint 30 may include one or more structures for releasably securing the access device 330 to the dissector 20. For example, as shown, the constraint includes a plurality of fingers 31 extending from an inner collar or sleeve that may engage a proximal end of the access device 330 and an outer sleeve 34 or other structure that may press the fingers 31 inwardly to hold the access device 330 relative to the dissector 20, e.g., to prevent the access device 330 from rotating and/or sliding axially relative to the distal end 24. In an exemplary embodiment, the outer sleeve 34 may be advanced to compress the fingers 31 to apply an inward force between the access device 330 and the outer surface of the distal end portion 24, e.g., to frictionally secure the access device 330 to the distal end portion 24. The sleeve 34 may be retracted to remove the force from the fingers 30, thereby removing the friction or other force between the access device 330 and the dissector 20, e.g., to allow the dissector 20 to be withdrawn proximally relative to the access device 330.

Optionally, as shown in FIG. 5B, the constraint 30 may include one or more stops 32, e.g., on an inner surface of one or more (e.g., each) of the fingers 31, to prevent proximal migration when the distal end portion 24 of the dissector 20 is removed proximally from within the access device 330. For example, a plurality of tabs or ridges 32 may be provided on inner surfaces of the fingers 31, which may abut the proximal end of the access device 330. Thus, if the dissector 20 is removed, e.g., after positioning the dissector 20 and access device 330 around a body structure, the proximal end of the access device 330 may contact the tabs or ridges 32, thereby maintaining the access device 330 substantially in place around the body structure. The access device 330 may thus slide off the distal end portion 24 and be received around the body structure.

Alternatively, other constraints may be provided on the dissector 20 to releasably secure and/or prevent proximal migration of the access device 330. For example, an outer sleeve, e.g., having a "C" shaped cross-section (not shown) may be provided over the access device 330, e.g., including a stop to allow withdrawal of the dissector 20. In another embodiment, one or more filaments (not shown) may be wrapped around the access device 330 and/or dissector 20 to secure the access device 330. The filament(s) may be cut or otherwise removed, e.g., to release the access device 330 and/or allow removal of the dissector 20.

During use, the access device 330 may be loaded or otherwise provided on the distal end portion 24 of the dissector 20. In one embodiment, the access device 330 may have an inner diameter and/or a perimeter smaller than the distal end portion 24, e.g., such that longitudinal edges 336 of the access device 330 do not extend entirely around the distal end portion 24, for example, offset from the longitudinal edges 27 of the dissector 20, as shown in FIG. 5C. For example, the access device 330 may apply a radially inward force against the outer surface of the distal end portion 24. Alternatively, the access device 330 may have an inner diameter similar to the outer diameter of the distal end portion 24 such that the access device 330 is in a substantially relaxed condition around the distal end portion 24.

The distal end portion 24, carrying the access device 330, e.g., secured by the constraint 30, may be introduced into a patient's body to implant the access device 330. For example, the distal end portion 24 may be introduced directly through a percutaneous incision or other opening in the patient's skin towards a target location, e.g., a body structure beneath the skin, such as a blood vessel, fistula, or tubular graft (not shown). Alternatively, the distal end portion 24 may be introduced through another device previously placed between the patient's skin and the target location, e.g., an endoscope, introducer sheath, and the like (not shown).

A portion of the body structure may be received through the slot between the longitudinal edges 27 into an interior 28 of the dissector 20, e.g., to position the access device 330 around the body structure. If the slot has a smaller width than the body structure, the distal end portion 24 may be directed around the body structure with the longitudinal edges 27 opening to accommodate receiving the body structure through the slot into the interior 28. The distal end portion 24 may be sufficiently flexible to allow the distal tip 26 to contact the body structure at an angle, thereby opening the slot at the tip 26 and then opening the slot proximally along the distal end portion 24 as the body structure passes through the slot.

The distal end portion 24 may be advanced along the body structure, e.g., to dissect adjacent tissue from an outer surface of the body structure, e.g., to provide a portion of the body structure free from tissue adhesions or other undesired materials on its outer surface. In this manner, the distal end portion 24 may be advanced and/or otherwise manipulated to position the access device 330 over or around a desired section of the body structure.

The dissector 20 may then be removed, to release the access device 330 around the body structure. For example, as described above, the constraint 30 may be removed or otherwise actuated to release the access device 330 from the distal end portion 24, whereupon the dissector 20 may be withdrawn proximally along the body structure while the access device 330 remains substantially in place around the body structure. Once the dissector 20 is removed from within the access device 330, the dissector 20, constraint 30, and/or other components of the apparatus 10 may be removed, leaving the access device 330 in place. Optionally, the access device 330 may be further secured to the body structure, e.g., using one or more of sutures, adhesives, and the like, as described elsewhere herein and in the applications incorporated by reference herein.

A number of methods can be used to make the access devices described herein and in the applications incorporated by reference herein. For example, FIGS. 7A-7C show an exemplary method for making an elastic element in the form of a ring that may be included in an access device, such as the cuff of FIGS. 2A-2C. As shown in FIG. 7A, an elongate cylindrical mandrel 100 may be provided that includes multiple sets of pins 110 arranged in a predetermined pattern around the periphery of the mandrel 100, e.g., including a first annular set, a second annular set offset axially from the first annular set, a third set, and the like.

A wire or other filament or strand 120 (e.g., formed from Nitinol or other material, as described elsewhere herein) may be wound around a first set of pins 110 of the mandrel 100, e.g., circumferentially in a zigzag pattern, and then offset to and wound around a second set of pins, etc., based on the number of sets of pins 110 provided on the mandrel 100. The winding may be repeated to provide a tubular structure 122 including a plurality of annular rings 150 of zigzag elements spaced apart axially from one another.

Optionally, the tubular structure 122 may be heat treated or otherwise further processed while remaining on the mandrel 100. In this option, the mandrel 100 should be formed from materials able to withstand any processing parameters. Once a desired number of rings 150 have been formed (corresponding to the number of sets of pins 110), the tubular structure 122 may be removed from the mandrel 100. For example, given the elasticity of the strand 120, the tubular structure 122 may simply be elastically stretched and pulled off from around the pins 110 and mandrel 100. Alternatively, the pins 110 may be removable or retractable into the mandrel 100 (not shown) to accommodate removal after forming the tubular structure 122.

Turning to FIG. 7B, the tubular structure 122 of FIG. 7A may be separated into a plurality of rings of zigzag elements (one ring 150 shown) including free ends. For example, the wire 120 may be cut or otherwise severed between each ring 150 and any portions of the wire 120 defining connectors between each ring 150 and any excess beyond the last rings may be severed, thereby providing multiple separate rings 150, each with free ends 152, as shown in FIG. 7B. As shown in FIG. 7C, the free ends 152 of each ring 150 may be attached together, e.g., by being inserted and crimped in a hypotube or other sleeve 154, or alternatively by welding, bonding with adhesive, and the like (not shown). The resulting ring(s) 150 may be heat treated, further processed, and/or incorporated into an access device (not shown), as described elsewhere herein and in the applications incorporated by reference herein. Alternatively, the tubular structure 122 may be incorporated into an access device without separating the individual rings 150.

For example, the individual ring(s) 150 (or entire tubular structure 122) may be embedded in or otherwise combined with a base material to provide a tubular sleeve for an access device, e.g., using the methods described elsewhere herein. Optionally, the resulting tubular sleeve may be cut longitudinally, e.g., to provide a cuff or may be used to form a tubular access device, as described elsewhere herein. Alternatively, the ring(s) 150 shown in FIG. 7B may be used without attaching the free ends 152. For example, the ring(s) 150 may be shape set in a "C" shape, a curved shape, or a substantially flat shape with the free ends 152 spaced apart, e.g., corresponding to a desired diameter or other shape of an access device (not shown), and may be embedded in or otherwise combined with base material, e.g., using the methods described elsewhere herein. Thus, the free ends 152 may be disposed along longitudinal edges of an access cuff or other access device.

A similar process may be used for forming substantially flat or arcuate elastic elements. For example, a substantially flat or curved mandrel may be provided with multiple set of pins (not shown) arranged in a predetermined pattern across a surface of the mandrel, e.g., including a first set, a second set offset axially from the first set, etc. A wire may be wound around the pins to provide adjacent zigzag elements connected and/or offset from one another, which may remain together or may be separated into separate zigzag elements for incorporation into an access device (not shown).

Figure 8:
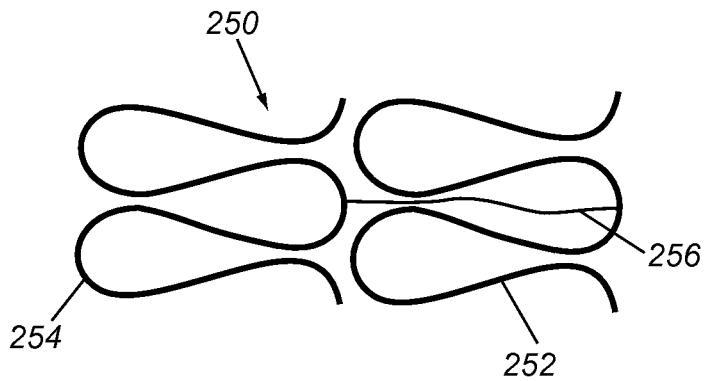
FIG. 8 is a detail of an exemplary embodiment of a mesh pattern for a set of elastic elements including a connector connecting adjacent bands that may be incorporated into an access device.

Turning to FIG. 8, a detail is shown of another exemplary embodiment of a mesh pattern for an access device (not shown) in which adjacent sets of elastic elements (e.g., rings) are connected to one another. As shown, the mesh pattern may include zigzag elements 250 adjacent one another with each zigzag element defining an enclosed or open ring or a substantially flat or curved elastic element with free ends (not shown). Similar to other embodiments, each zigzag element 250 may include substantially straight or generally longitudinal struts 252 connected at alternating ends by curved struts 254, thereby defining a serpentine or other zigzag pattern.

One or more connector elements 256 may couple adjacent sets of zigzag elements 250, e.g., extending between longitudinally adjacent curved struts 254, which may be thinner and/or more flexible than the struts 252, 254 of the elastic elements 250. In an exemplary embodiment, a single connector element 256 may connect adjacent zigzag elements 250. The connector element(s) 256 may be substantially straight having a length slightly greater than the distance between the adjacent curved struts 254 that are coupled together, or may have a curvilinear shape defining an overall length greater than the distance between the adjacent curved struts 254, e.g., providing additional flexibility and/or adjustability between the adjacent zigzag elements 250.

The connector element(s) 256 may allow a plurality of zigzag elements 250 to be fabricated together, e.g., by laser cutting, chemical etching, EDM, water jet, and the like. For example, a tube or sheet of material may have unwanted material removed to result in a desired arrangement of zigzag elements 250 and connector elements 256 that are integrally formed together. The connector elements 256 may provide substantially no structure, but may simply keep the zigzag elements 250 together during subsequent processing and/or incorporation into an access device (not shown). For example, during electro-polishing, the connector elements 256 may provide a conductive path allowing electrical current to pass between the zigzag elements 250, allowing all of the zigzag elements 250 to be processed together.

Thus, the zigzag elements 250 may be manually or otherwise manipulated together during processing, e.g., to set a shape and/or pre-stress the zigzag elements 250, as described elsewhere herein. After processing, the zigzag elements 250 may be incorporated into an access device, e.g., by embedding into base material, with the connector elements 256 remaining intact (but providing little limitation on subsequent movement of the zigzag elements 250 during use of the access device given their flexibility). The connector elements 256 may facilitate loading and/or positioning the zigzag elements 250 before or during incorporation into base material since the zigzag elements 250 remain coupled together yet may be adjusted relative to one another. The connector elements 256 may also be sufficiently flexible to accommodate adjusting the distance between adjacent zigzag elements 250, e.g., allowing the zigzag elements 250 to be partially nested together, if desired, during incorporation into the base material. Alternatively, the connector elements 250 may be severed and/or removed and individual zigzag elements may be incorporated into an access device, as described elsewhere herein.

Figure 9A:
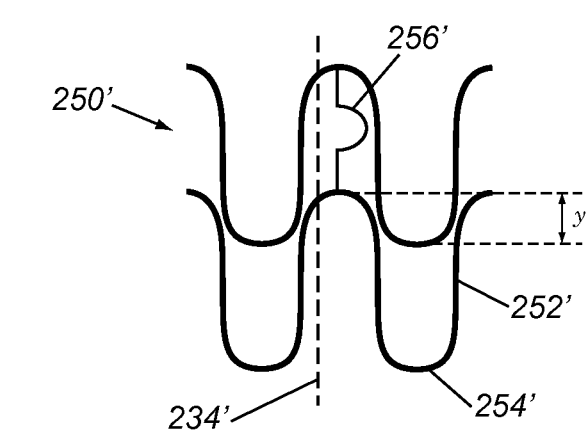
FIGS. 9A and 9B are details of another exemplary embodiment of a mesh pattern for a set of elastic elements including a connector connecting adjacent bands that may be longitudinally lengthened and shortened.
Figure 9B:
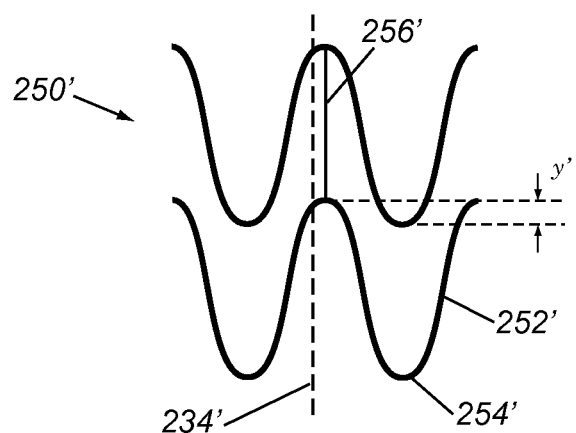

Turning to FIGS. 9A and 9B, details of another exemplary embodiment of a mesh pattern for an access device is shown in which adjacent sets of elastic elements (e.g., rings or other zigzag elements 250') are connected together. As shown, the mesh pattern may include zigzag elements 250' adjacent one another with each zigzag element defining an enclosed or open ring or a substantially flat or curved elastic element with free ends (not shown). Similar to other embodiments, each zigzag element 250' may include substantially straight or generally longitudinal struts 252' connected at alternating ends by curved struts 254,' thereby defining a serpentine or other zigzag pattern.

One or more connector elements 256' may couple adjacent zigzag elements 250,' e.g., extending between longitudinally adjacent curved struts 254.' For example, each curved strut 254' may be connected to the adjacent curved strut 254' by a connector element 256' to provide a closed-cell mesh, or only some (e.g., ever other, every third, etc.) of the curved struts 254' may be connected by a connector element 256' to provide an open-cell mesh.

The connector elements 256' may have an initial, relaxed shape, e.g., a curvilinear shape as shown in FIG. 9A, and may be resiliently manipulated to a pre-stressed shape, e.g., a substantially straight shape as shown in FIG. 9B. For example, the sets of elastic elements 250' may be extended along a longitudinal axis 234' of the resulting access device to increase the overall length of the elastic elements 250,' e.g., to provide a longitudinal pre-stress when the elastic elements 250' are incorporated into an access device. In addition or alternatively, the sets of elastic elements 250' may be expanded radially, circumferentially, or otherwise transverse to the longitudinal axis 234,' similar to other embodiments herein, thereby pre-stressing the elastic elements 250' laterally, e.g., to bias the elastic elements 250' towards a smaller diameter or lateral length.

In the pre-stressed condition, e.g., with the connector element(s) 256' at least partially straightened as shown in FIG. 9B, adjacent elastic elements 250' may remain partially nested with each other, e.g., such that there is overlap between the nearest curved struts 254 of the adjacent elastic elements 250.' When the connector element(s) 256' are released, e.g., after being embedded into base material or otherwise incorporated into an access device, the connector element(s) 256' may bias the adjacent elastic elements 250' towards the nested position, such as that shown in FIG. 9A. Optionally, the thickness of the struts 252,' 254,' 256' and/or the radius of the curved struts 254' may be adjusted, as desired, to modify the stiffness and/or bias of the resulting access device.

Any of the elastic elements described herein and in the applications incorporated by reference herein may be embedded or otherwise incorporated into base material and covered with fabric or other covering to provide an access device. In one method, the elastic elements may be placed within a mold and base material injected into the mold to encase the elastic elements in the base material.

Figure 10A:
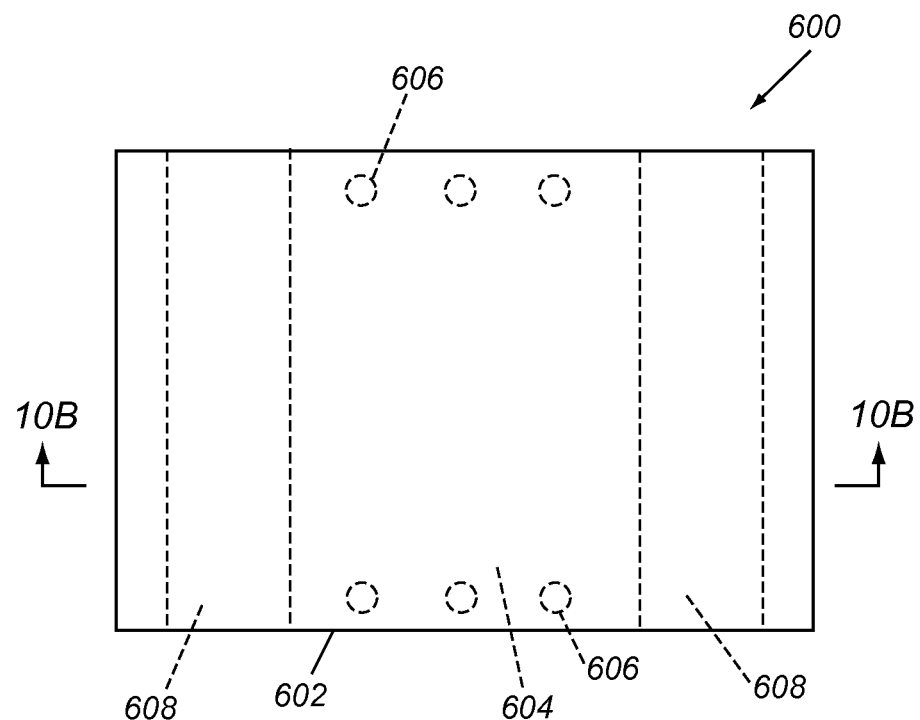
FIGS. 10A and 10B are top and cross-sectional views, respectively, of a flat mold including a cavity within which a set of elastic elements have been mounted for making a substantially flat access device.
Figure 10B:
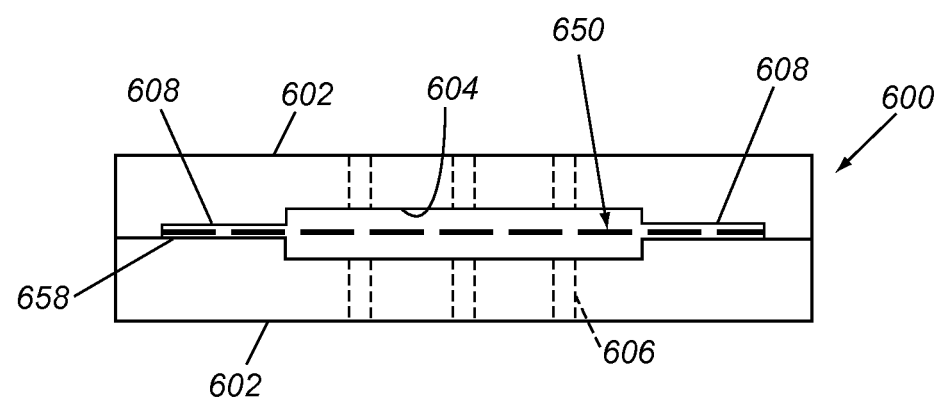

For example, turning to FIGS. 10A and 10B, an exemplary embodiment of a flat mold 600 is shown that includes a pair of mold plates 602 defining a cavity 604 therebetween within which a set of elastic elements 650 have been mounted, e.g., under tension or other pre-stressed state, or in a relaxed state. As shown, extended ends 658 of the set of elastic elements 650 may be secured within end regions 608 of the mold 600 such the elastic elements 650 are suspended or otherwise arranged within the cavity 604 as desired.

Elastomer or other base material (not shown) may be injected into the cavity 604, e.g., via injection ports 606, to encase the elastic elements 650 and create a panel for an access device (e.g., after securing a fabric covering around the panel, not shown), similar to other embodiments herein and in the applications incorporated by reference herein. As shown, the mold 600 may include multiple injection ports 606, e.g., at each end of the cavity 604 and/or in one or both mold plates 602, which may reduce time to inject the base material and/or provide substantial uniformity when filling the cavity 604. The depth of the recesses defining the cavity 604 in the mold plates 602 may be selected to provide a desired thickness for the resulting access device, which may be substantially uniform or may variable, as desired. Once the base material is injected and cured, as desired, the mold plates 602 may be opened, and the encased elastic elements 650 removed and processed further to provide the final access device (not shown), e.g., removing the extended ends 658, adding a fabric covering (not shown), and the like.

Turning to FIGS. 11A and 11B, an embodiment of a cylindrical mold 700 is shown including a plurality of mold plates 702, 703 defining an annular cavity 704 within which a set of elastic elements 750 have been mounted, e.g., under tension or otherwise pre-stressed, similar to other embodiments herein. For example, the set of elastic elements 750 may include extended ends 758 that may be secured within end regions 708 of the mold 700, e.g., similar to the flat mold 600 of FIGS. 10A and 10B.

As best seen in FIG. 11B, the mold 700 may include a hollow mold core 702 including a passage 702a communicating with injection ports 706 that, in turn, communicate with the interior of the cavity 704. The mold 700 also includes one or more outer mold plates 703, e.g., a pair of plates that may be secured around the core 702 and the set of elastic elements 750, recesses of the core 702 and plates 703 together defining the cavity 704.

Elastomeric or other base material (not shown) may be injected into the cavity 704 via the core passage 702a and injection ports 706, to encase the elastic elements 750 and create a sleeve for an access device (not shown), similar to other embodiments herein and in the applications incorporated by reference herein. The elastic elements 750 may be mounted within the cavity 704 in a substantially relaxed state or in a pre-stressed state, e.g., resiliently radially expanded and/or longitudinally stretched across the cavity 704 to pre-stress the elastic elements 750 in a desired manner when encased in the elastomeric material. Alternatively, a multiple step molding process may be used, e.g., to first create a base layer (not shown) either inside or outside the elastic elements 750, which may support the elastic elements 750, e.g., to maintain a substantially uniform diameter or other configuration. In a further alternative, the elastic elements 750 may be mounted on an elastomeric base (also not shown), e.g., on an outer surface of an elastomeric tube, which may be mounted across the cavity to allow one or more additional layers to be injected and formed around the elastic elements 750 and base material.

In addition to molding, other methods may be used for encasing or otherwise incorporating elastic elements into base material to provide an access device, such as those described elsewhere herein. For example, one or more sheets, cylinders, or other configurations of base material may be formed and elastic elements may be embedded into and/or otherwise attached to the base material.

Turning to FIGS. 12A-12D, exemplary methods are shown for embedding a set of elastic elements 850 into a sheet 832 of elastomeric or other base material. For example, as shown in FIGS. 12A and 12B, the elastic elements 850 may be formed and positioned in a desired arrangement, e.g., with a plurality of individual or connected zigzag elements disposed adjacent one another, e.g., in a relaxed or pre-stressed state and/or nested or spaced apart, as shown in FIG. 12A. A sheet 832 of base material may then be applied over the elastic elements 850, as shown in FIG. 12B.

Figure 13A:
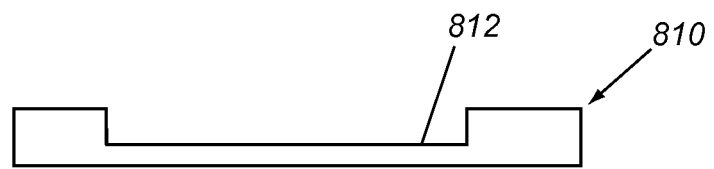
FIGS. 13A-13C are cross-sectional views of a mold showing another exemplary method for making an access device.
Figure 13B:
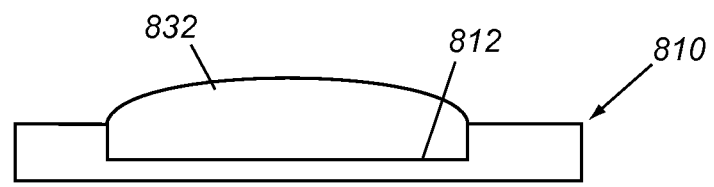
Figure 13C:
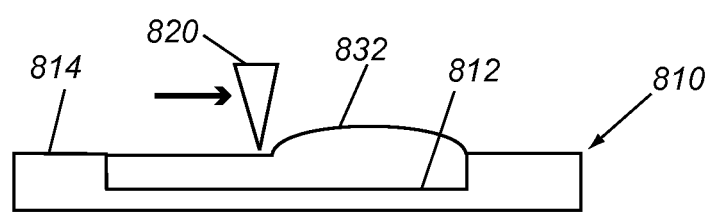

For example, a solid, cured sheet 832 of base material may be applied and/or attached to the elastic elements 850. Optionally, one or more additional layers of base material (not shown) may be applied to the base material 832 over the elastic elements 850, e.g., by bonding with adhesive, fusing, reflowing, and the like, to encase the elastic elements 850 within the base material. Alternatively, the elastic elements 850 may be placed within a tray or other receptacle (not shown), and uncured or otherwise flowable base material 832 may be poured over the elastic elements 850 into the receptacle to encase the elastic elements 850 therein, e.g., as shown in FIGS. 13A-13C and described further below, whereupon the base material 832 may be cured, cross-linked, and/or otherwise processed.

In a further alternative, as shown in FIGS. 12C and 12D, a sheet or other substrate 832 of base material may be formed, and then a set of elastic elements 850 may be placed within the substrate 832. For example, as shown in FIGS. 13A-13C, base material may be mixed or otherwise prepared such that the base material remains at least partially uncured, e.g., such that the base material remains in a liquid, gel, or other flowable state (not shown). A tray or other receptacle 810 may be provided that includes a recess or depression 812 therein into which the flowable base material 832 may be poured, as shown in FIG. 13B. Any excess base material 832 may be removed, e.g., using a blade or other tool 820 that is directed along a top surface 814 of the receptacle 810 to provide a substantially planar exposed surface for the base material 832. Once the excess material is removed, the elastic elements 850 may then be inserted into the base material, as shown in FIG. 12D, e.g., in a relaxed or pre-stressed state, similar to other embodiments herein. The base material 832 may then be cured, cross-linked, and/or other processed, e.g., to encase the elastic elements 850 within the fully cured base material 832.

Alternatively, the base material 832 may be fully cured and then the elastic elements 850 may placed on the base material 832 or inserted into the base material 832, e.g., forced into, heated to melt or reflow the base material 832 around the elastic elements 850, and the like. Alternatively, a "negative pattern" may be created in the exposed surface of the base material 832, e.g., using a stamp or other tool (not shown) inserted into the exposed surface of the uncured base material 832. The base material may then be cured, cross-linked, and/or otherwise processed and the tool removed to create a set of recesses corresponding to the configuration of the struts of the elastic elements 850. Thus, the elastic elements 850 may be received in the preformed recesses rather than forced directly into the base material 832. Optionally, one or more additional layers of base material (not shown) may be applied over and/or otherwise fused or attached to the base material 832, thereby encasing the elastic elements 850.

In yet another alternative, a spray/thin film deposition method may be used to form the base material. For example, one or more layers of elastomeric material may be sprayed in a liquid or powder form, e.g., within a tray or other receptacle (not shown). Exemplary spraying methods may include aerosol sprays, electrostatic charge deposition (e.g., powder coating, copier ink/toner application), ink jet deposition technology, and the like. After application of the elastomeric material, additional steps may be taken to cure, cross-link, and/or otherwise process the base material (e.g., by applying one or more of heat, humidity, visible or ultraviolet light, and the like). In one embodiment, elastomeric material may be deposited over a die stamp, which creates an impression of the configuration of the elastic elements 850 in its lower surface (not shown). When the stamp is removed, the resulting base material 832 may include a recess pattern corresponding to the configuration of the elastic elements 850. This may eliminate any need for additional fixturing to position the elastic elements 850 since they may nest into the recess pattern, which may also improve device-to-device consistency. For ink jet deposition methods, a recess pattern for the elastic elements 850 may be created directly, e.g., as the base material is deposited.

In addition, the recess pattern may be selected such that the elastic elements 850 are stressed when inserted into the recesses. For example, the recess pattern may include recesses corresponding to each of the struts of the elastic elements 850, but the recesses may be spaced apart from a relaxed state of the elastic elements 850. Thus, the recess pattern and the base material surrounding the recesses may retain the elastic elements 850 in a pre-stressed state without requiring additional fixturing. Optionally, in these methods, after the elastic elements 850 have been positioned in the recess pattern, a final layer of base material may be applied to completely embed or otherwise encase the elastic elements 850.

In still another alternative, a dip method may be used to create the base material. For example, one or more layers of elastomeric material may be applied over a mandrel (not shown), e.g., by dipping the mandrel one or more times into the elastomeric material, e.g., in a liquid form. The thickness of the resulting base material may be controlled by one or more of the viscosity of the liquid elastomer, percent solids content of the elastomer, and/or number of dip applications. Another method to control the thickness is to dip a pair of parallel plates into the liquid solution, e.g., thereby forming a layer of base material between the plates that has a thickness corresponding to the spacing of the plates.

Turning to FIGS. 14A-14C, another method is shown for making an elastic member or panel 1030 for an access device by thermally welding a plurality of sheets or layers of base material 1030 around a set of elastic elements 1050. For example, as shown in FIG. 14A, a pair of sheets 1010 of elastomeric material may be provided, e.g., formed from any of the methods described elsewhere herein, either with or without recess patterns (not shown) corresponding to the elastic elements 1050.

The elastic elements 1050 may be positioned between the sheets 1010, and one or more of energy, pressure, and the like may be applied to weld the two sheets 1010 together and/or embed the elastic elements 1050 into the sheets 1010, e.g., resulting in the assembly 1028 shown in FIG. 14A. Energy may be applied directly, e.g., using heating elements (not shown), and/or indirectly, e.g., using one or more of radiofrequency (RF) electrical energy, ultrasonic vibration, and friction, e.g., to concentrate the energy at the interface between the sheets 1010. For example, the material of the elastic elements 1050 may act as an energy director that concentrates the resultant thermal energy at the inner surfaces of the sheets 1010 to promote embedding the elastic elements 1050 into and/or between the sheets 1010.

Optionally, as shown in FIG. 14B, a die 1020 may be used to apply the energy and/or form the assembly 1028 into a finished elastic sheet 1030 that may be incorporated into an access device (not shown). As shown, the die 1020 may include opposing plates 1022, 1024 that may include one or more heating elements and/or sources of other energy (not shown). For example, the upper plate 1022 may include a heating element (not shown), or may be configured as a cathode for RF welding and the lower plate 1024 may be configured as an anode for RF welding.

The components of the assembly 1028 may be positioned between the plates 1022, 1024, e.g., placing in sequence a first layer of base material 1010, the elastic elements 1050 (relaxed or pre-stressed), and a second layer of base material 1010 (shown in FIG. 14A) on the lower plate 1024, and the plates 1022, 2024 may then be directed together to apply pressure and/or other energy to the base material 1010 to attach them together, as described elsewhere herein. Optionally, the plates 1022, 1024 may include one or more blades or other cutting elements 1026 and opposing recesses 1027 arranged on respective the plates 1022, 1024 to cut the assembly 1028 into the final elastic panel 1030, e.g., as shown in FIG. 14C. The cutting element(s) 1026 may be fixed or may be mechanically actuated, e.g., using one or more springs, pneumatics, hydraulics, and the like (not shown) to press the cutting element(s) 1026 into and through the assembly 1028 (e.g., to enhance cutting through the base material 1032 and elastic elements 1050) into the opposing recess(es) 1027.

Figure 15A:
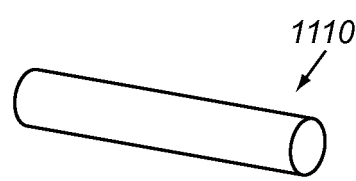
FIGS. 15A-15D are perspective views of a mold showing an exemplary method for making a generally cylindrical access device around the mold.
Figure 15B:
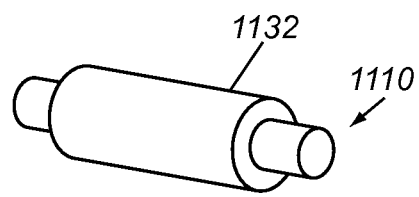

Turning to FIGS. 15A-15D, another method is shown for making an access device using a mandrel 1110, as shown in FIG. 15A, which may define the inner diameter of the resulting access device. The mandrel 1110 may be a solid or hollow cylindrical body formed from materials able to withstand the processing used and/or to provide a desired outer surface finish. Initially, as shown in FIG. 15B, a first layer of elastomeric or other base material 1032 may be provided around the mandrel 1110, e.g., by creating a first layer of base material directly on the mandrel 1110, or by wrapping a sheet of base material around the mandrel 1110, as shown in FIG. 15B. For example, the mandrel 1110 may be dipped in uncured, liquid base material, similar to other embodiments herein, with the thickness of the resulting coating controlled by one or more of viscosity of the liquid elastomer, percent solids content, and number of dip applications. Uniformity of application may also be enhanced by positioning the mandrel 1110 substantially horizontally after dipping and rotating the mandrel 1110 during curing.

Figure 16:
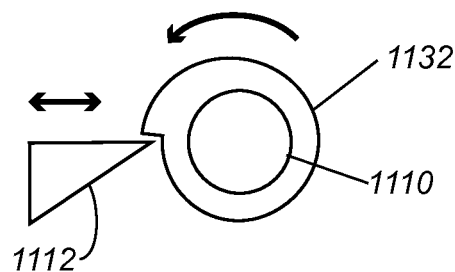
FIG. 16 is a cross-sectional view of a mold showing another exemplary method for making a generally cylindrical access device around the mold.

Alternatively, as shown in FIG. 16, a first layer of base material 1132 may be applied around the mandrel 1110 while rotating the mandrel 1110 and using a blade or other tool 1112 to remove excess base material. For example, uncured, liquid base material may be applied to the outer surface of the mandrel 1110 as it rotates, e.g., by spraying, brushing, and the like, and the tool 1112 may remove excess material such that the first layer 1132 achieves a desired outer diameter. Optionally, the material may cure as the mandrel 1110 is rotated, e.g., substantially continuously applying and curing the base material, e.g., by applying heat or other parameters to initiate curing as the base material is applied, until the desired outer diameter is achieved.

In another alternative, base material (e.g., thermoset or thermoplastic material) may be extruded through a die (not shown) over the mandrel 1110 directly, or may be extruded over beading or other subassembly (not shown) before being transferred to the mandrel 1110.

In still another alternative, a cylinder may be formed over the mandrel 1110 by wrapping a thin sheet or layer of flat base material with attached elastic elements (not shown, e.g., formed similar to other embodiments herein, such as the methods shown in FIGS. 12-13) around the mandrel 1110, and attaching the ends of the sheet together, e.g., by bonding with adhesive, fusing, mechanical connectors, sutures (not shown), and the like.

Figure 15C:
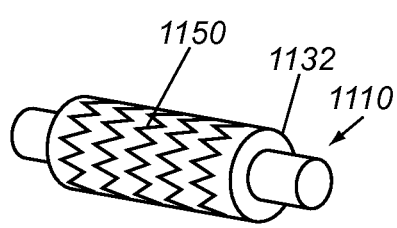
Figure 15D:
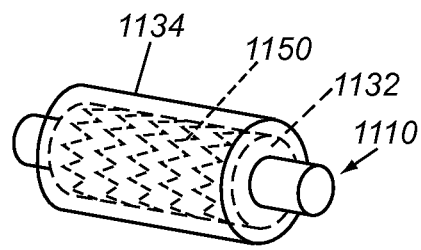

Once the base material 1132 is formed and/or secured on the mandrel 1110, a set of elastic elements 1150 may be positioned around the first layer 1132 or placed into the surface of the first layer 1132 if not already applied. For example, a recess pattern may be formed in the outer surface of the first layer 1132, e.g., by laser cutting, mechanical cutting, heating a stamp with the pattern (not shown), and the like into the outer surface. Alternatively, the elastic elements 1150 may be forced, heated, and/or otherwise directed into the outer surface, as shown in FIG. 15C.

Finally, a second layer of base material 1134 may be applied around the elastic elements 1150, e.g., by again creating the second layer 1134 directly on the mandrel 1110 (e.g., by dipping and curing, spraying and curing, and the like) or wrapping a sheet of base material around the mandrel 1110. For example, the second layer 1134 may be applied using the spray-on method shown in FIG. 16, forming and rolling a layer of base material, and the like to encase the elastic elements 1150.

Optionally, the resulting assembly may be processed further, e.g., to further cure or cross-link the base material, heat or fuse the layers, and the like. The mandrel 1110 may then be removed and the assembly incorporated into an access device, such as that shown in FIGS. 2A-2C. Optionally, additional base material may be added, e.g., using any combination of the other methods described herein, to reinforce the cylindrical shape after the mandrel 1110 is removed.

Figures 17A, 17B, 17C:
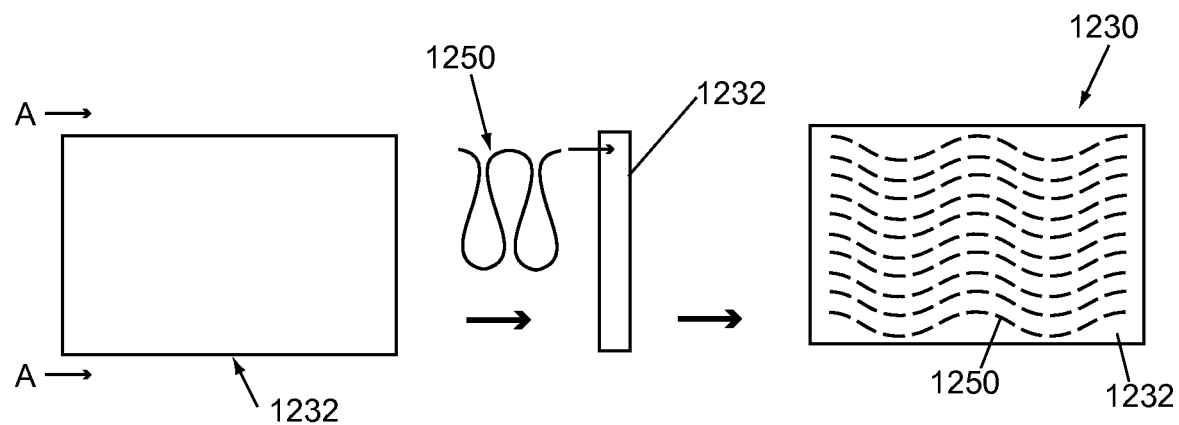
FIGS. 17A-17C show another exemplary method for making an access device including a set of elastic elements embedded in base material.

Turning to FIGS. 17A-17C, another method is shown for forming a sheet of elastic material 1230, e.g., including a plurality of elastic elements 1250 embedded in base material 1232. FIGS. 17A and 17B show front and end views of a sheet or layer of elastomeric material, similar to any of the other embodiments herein. A plurality of elastic elements 1250, e.g., individual curvilinear wires or other filaments, may be threaded from one edge of the sheet 1232 into and through the elastomeric material, as shown in FIG. 17B, to the opposite edge, e.g., as shown in FIG. 17C. Alternatively, a plurality of tubular guides, e.g., having straight or curvilinear shapes (not shown) may be placed through the sheet 1232 from one edge to the opposite edge, and the filaments 1250 may be threaded through the guides, which may then be removed. In this alternative, the filaments 1250 may have a different relaxed shape than the guides, such that the filaments 1250 become pre-stressed within the elastomeric sheet 1232 once the guides are removed.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the devices described herein may be combined with any of the delivery systems and methods also described herein.

While embodiments of the present invention have been shown and described, various modifications may be made without departing from the scope of the present invention. The invention, therefore, should not be limited, except to the following claims, and their equivalents.

We claim:

1. A method for making an access device, comprising:
    creating a plurality of zigzag bands disposed adjacent one another and one or more flexible connectors extending between adjacent zigzag bands, the flexible connectors biased to an original curvilinear shape aligned along a longitudinal axis;
    elastically lengthening and at least partially straightening the curvilinear shape the flexible connectors along the longitudinal axis to a stressed state, thereby increasing spacing between the adjacent zigzag bands;
    embedding the zigzag bands within a base material with the flexible connectors in the stressed state; and
    releasing the zigzag bands whereupon the flexible connectors are biased to return towards original the curvilinear shape, thereby pre-stressing the base material in a longitudinal direction along the longitudinal axis.

2. A method for making an access device, comprising:
    creating a plurality of elongate zigzag members, each zigzag member defining a longitudinal axis extending between opposite ends thereof, each zigzag member comprising a plurality of zigzag elements lying within a plane and extending between the opposite ends along the longitudinal axis in an original curvilinear shape;
    elastically lengthening the zigzag members along the longitudinal axis to at least partially straighten the zigzag elements to a stressed state;
    embedding the zigzag members within a base material in the stressed state; and
    releasing the zigzag members whereupon the zigzag elements are biased to return towards the original curvilinear shape, thereby pre-stressing the base material in a longitudinal direction along the longitudinal axis.

3. The method of claim 2, wherein the zigzag members are created in a cylindrical shape defining a relaxed diameter such that the zigzag members lie within a curved plane extending around a circumference of the cylindrical shape, the method further comprising:
    mounting the zigzag members within a cavity of a mold;
    elastically expanding the zigzag members from the relaxed diameter to an expanded diameter;
    injecting base material into the cavity to encase the zigzag members therein, wherein the zigzag members are mounted within the cavity in the expanded diameter when the base material is injected into the cavity; and
    releasing the zigzag members from the expanded diameter whereupon the zigzag members are biased towards the relaxed diameter to pre-stress the base material.

4. The method of claim 2, wherein the zigzag members are created in a planar shape, and wherein embedding the zigzag members within a base material comprises:
    placing the zigzag members within a cavity of a receptacle;
    applying material within the cavity to encase the zigzag members therein and excess base material is disposed over the zigzag members and extends out of the cavity; and
    removing the excess material.

5. The method of claim 2, wherein, upon releasing, the zigzag members impose a substantially continuous compressive force on the adjacent base material along the longitudinal axis to enhance sealing any passages created through the base material.

6. The method of claim 2, wherein the access device has a generally "C" shaped cross-section including longitudinal edges extending parallel to the longitudinal axis.

7. The method of claim 2, wherein embedding the zigzag members comprises:
    mounting the zigzag members within a cavity of a mold; and
    injecting base material into the cavity to encase the zigzag members therein.

8. The method of claim 7, wherein the zigzag members are created in a planar shape lying within the plane defining a relaxed configuration, the method further comprising:
elastically expanding the zigzag members within the plane from the relaxed configuration to an expanded configuration defining the stressed state, and wherein the zigzag members are mounted within the cavity in the expanded configuration when the base material is injected into the cavity; and
releasing the zigzag members from the expanded configuration whereupon the zigzag members are biased towards the relaxed configuration to pre-stress the base material.

9. The method of claim 2, wherein the zigzag members are created in a planar shape, and wherein embedding the zigzag members within the base material comprises:
applying base material in a liquid or uncured viscous state within a receptacle;
placing the zigzag members such that the zigzag members are on or in the base material within the receptacle; and
curing the base material to embed the zigzag members therein.

10. The method of claim 9, further comprising removing excess base material from the receptacle before placing the zigzag members on or in the base material.

11. A method for making an access device, comprising:
creating a plurality of elongate zigzag members defining a longitudinal axis, each zigzag member comprising a plurality of zigzag elements lying within a plane and extending along the longitudinal axis in an original curvilinear shape;
elastically lengthening the zigzag members to at least partially straighten the zigzag elements to a stressed state;
embedding the zigzag members within a base material in the stressed state; and
releasing the zigzag members whereupon the zigzag elements are biased to return towards the original curvilinear shape, thereby pre-stressing the base material in a longitudinal direction,
wherein the zigzag members are created in a planar shape, and wherein embedding the zigzag members within a base material comprises:
creating a planar first layer of base material;
inserting the zigzag members into a surface of the first layer;
rolling the first layer and zigzag members around a mandrel; and
applying a second layer of base material around the zigzag members and first layer around the mandrel.

12. A method for making an access device, comprising:
creating a plurality of elongate zigzag members defining a longitudinal axis, each zigzag member comprising a plurality of zigzag elements lying within a plane and extending along the longitudinal axis in an original curvilinear shape;
elastically lengthening the zigzag members to at least partially straighten the zigzag elements to a stressed state;
embedding the zigzag members within a base material in the stressed state; and
releasing the zigzag members whereupon the zigzag elements are biased to return towards the original curvilinear shape, thereby pre-stressing the base material in a longitudinal direction,
wherein the zigzag members are created in a planar shape, and wherein embedding the zigzag members within a base material comprises:
creating a planar first layer of base material over a die stamp including a pattern corresponding to the shape of the zigzag members;
removing the die stamp to expose the pattern of features corresponding to the pattern on the die stamp;
placing the zigzag members on the first layer such that the zigzag members are engaged with the features; and
applying a second layer of base material over the zigzag members and first layer.

13. The method of claim 12, wherein the features are recesses in an exposed surface of the base layer, and wherein placing the zigzag members on the first layer comprises placing the zigzag members such that the zigzag members are received within the recesses.

14. The method of claim 12, wherein the features extend outwardly from the first surface, and wherein placing the zigzag members on the first layer comprises placing the zigzag members at least partially around the features.

* * * * *